US010291977B2

(12) United States Patent
Mackellar et al.

(10) Patent No.: US 10,291,977 B2
(45) Date of Patent: May 14, 2019

(54) METHOD AND SYSTEM FOR COLLECTING AND PROCESSING BIOELECTRICAL AND AUDIO SIGNALS

(71) Applicant: Emotiv, Inc., San Francisco, CA (US)

(72) Inventors: Geoffrey Mackellar, San Francisco, CA (US); Tan Le, San Francisco, CA (US)

(73) Assignee: Emotiv Inc., San Francisco, CA (US)

( * ) Notice: Subject to any disclaimer, the term of this patent is extended or adjusted under 35 U.S.C. 154(b) by 350 days.

(21) Appl. No.: 15/209,582

(22) Filed: Jul. 13, 2016

(65) Prior Publication Data

US 2017/0041699 A1    Feb. 9, 2017

Related U.S. Application Data

(60) Provisional application No. 62/201,256, filed on Aug. 5, 2015.

(51) Int. Cl.
| | |
|---|---|
| *A61B 5/04* | (2006.01) |
| *A61B 5/0476* | (2006.01) |
| *H04R 1/10* | (2006.01) |
| *A61B 5/024* | (2006.01) |
| *A61B 5/048* | (2006.01) |

(Continued)

(52) U.S. Cl.
CPC ....... *H04R 1/1075* (2013.01); *A61B 5/02405* (2013.01); *A61B 5/048* (2013.01); *A61B 5/04012* (2013.01); *A61B 5/0476* (2013.01); *A61M 21/02* (2013.01); *H04R 1/105* (2013.01); *H04R 1/1091* (2013.01); *A61B 5/02438* (2013.01); *A61B 5/6816* (2013.01); *A61B 5/7203* (2013.01); *A61M 2021/0027* (2013.01); *G10L 25/63* (2013.01); *G10L 25/66* (2013.01)

(58) Field of Classification Search
None
See application file for complete search history.

(56) References Cited

U.S. PATENT DOCUMENTS

| | | | |
|---|---|---|---|
| 2007/0060831 A1* | 3/2007 | Le | A61B 5/0476 600/544 |
| 2009/0214060 A1 | 8/2009 | Chuang et al. | |

(Continued)

FOREIGN PATENT DOCUMENTS

| | | |
|---|---|---|
| JP | 2014215963 A | 11/2014 |
| WO | WO 2014150684 A1 * | 9/2014 ........... A61B 5/1103 |

OTHER PUBLICATIONS

Srinivasan et al. Heart Rate Calculation from Ensemble Brain Wave Using Wavelet and Teager-Kaiser Energy Operator. IEEE (2015).*

*Primary Examiner* — Etsub D Berhanu
(74) *Attorney, Agent, or Firm* — Jeffrey Schox; Diana Lin

(57) ABSTRACT

A method and system for detecting bioelectrical signals and audio signals from a user, including establishing bioelectrical contact between a user and one or more sensors of a biomonitoring neuroheadset; collecting, at the one or more sensors, one or more bioelectrical signal datasets; collecting one or more reference signal datasets; collecting, at a microphone of the biomonitoring neuroheadset, an audio signal dataset; and generating a combined audio and bioelectrical signal processed dataset, including producing a noise-reduced bioelectrical signal dataset, and producing a conditioned audio signal dataset.

20 Claims, 9 Drawing Sheets

(51) Int. Cl.
*A61M 21/02* (2006.01)
*G10L 25/63* (2013.01)
*A61M 21/00* (2006.01)
*G10L 25/66* (2013.01)
*A61B 5/00* (2006.01)

(56) References Cited

U.S. PATENT DOCUMENTS

| | | | |
|---|---|---|---|
| 2009/0259137 A1* | 10/2009 | Delic | A61B 5/0478 600/545 |
| 2010/0172522 A1 | 7/2010 | Mooring et al. | |
| 2010/0217100 A1 | 8/2010 | LeBoeuf et al. | |
| 2011/0196211 A1* | 8/2011 | Al-Ali | A61B 5/14551 600/300 |
| 2011/0270117 A1* | 11/2011 | Warwick | A61B 5/0476 600/544 |
| 2013/0317384 A1* | 11/2013 | Le | A61B 5/0482 600/545 |
| 2014/0316230 A1* | 10/2014 | Denison | A61B 5/04012 600/544 |
| 2014/0336473 A1 | 11/2014 | Greco | |
| 2015/0150753 A1 | 6/2015 | Racette | |

* cited by examiner

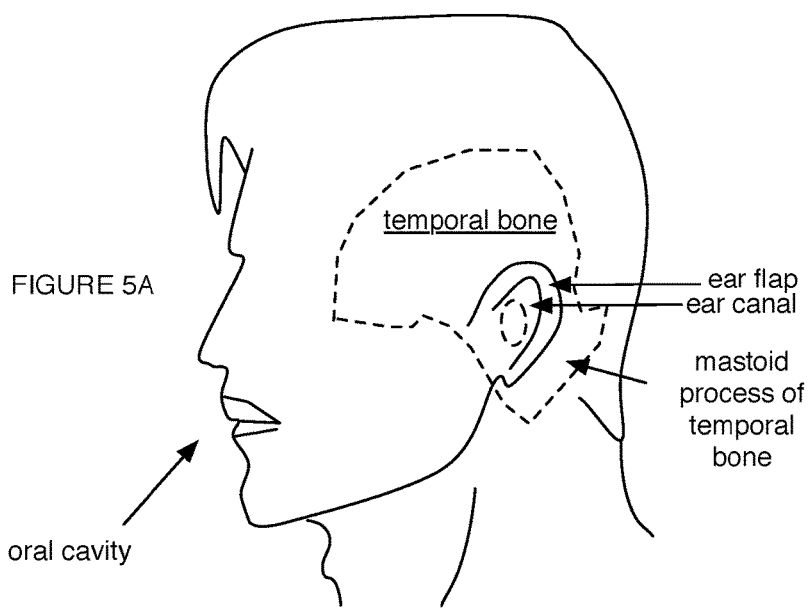
FIGURE 5A
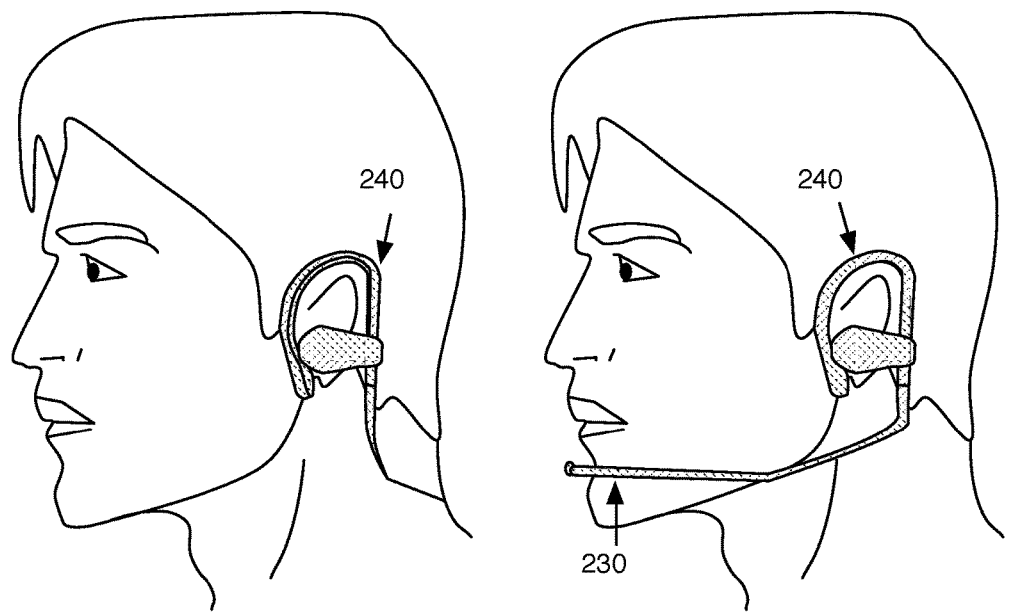
FIGURE 5B
FIGURE 5C

US 10,291,977 B2

METHOD AND SYSTEM FOR COLLECTING AND PROCESSING BIOELECTRICAL AND AUDIO SIGNALS

CROSS-REFERENCE TO RELATED APPLICATIONS

This application claims the benefit of U.S. Provisional Application Ser. No. 62/201,256 filed 5 Aug. 2015, which is incorporated in its entirety herein by this reference.

TECHNICAL FIELD

This invention relates generally to the field of digital signal collection and processing, and more specifically to a new and useful method and system for collecting, processing, and analyzing bioelectrical and audio signals.

BRIEF DESCRIPTION OF THE FIGURES

FIGS. 5A-5C depict graphical representations of user anatomical regions and variations of an embodiment of a system for detecting bioelectrical and audio signals of a user;

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview.

Figure 1:
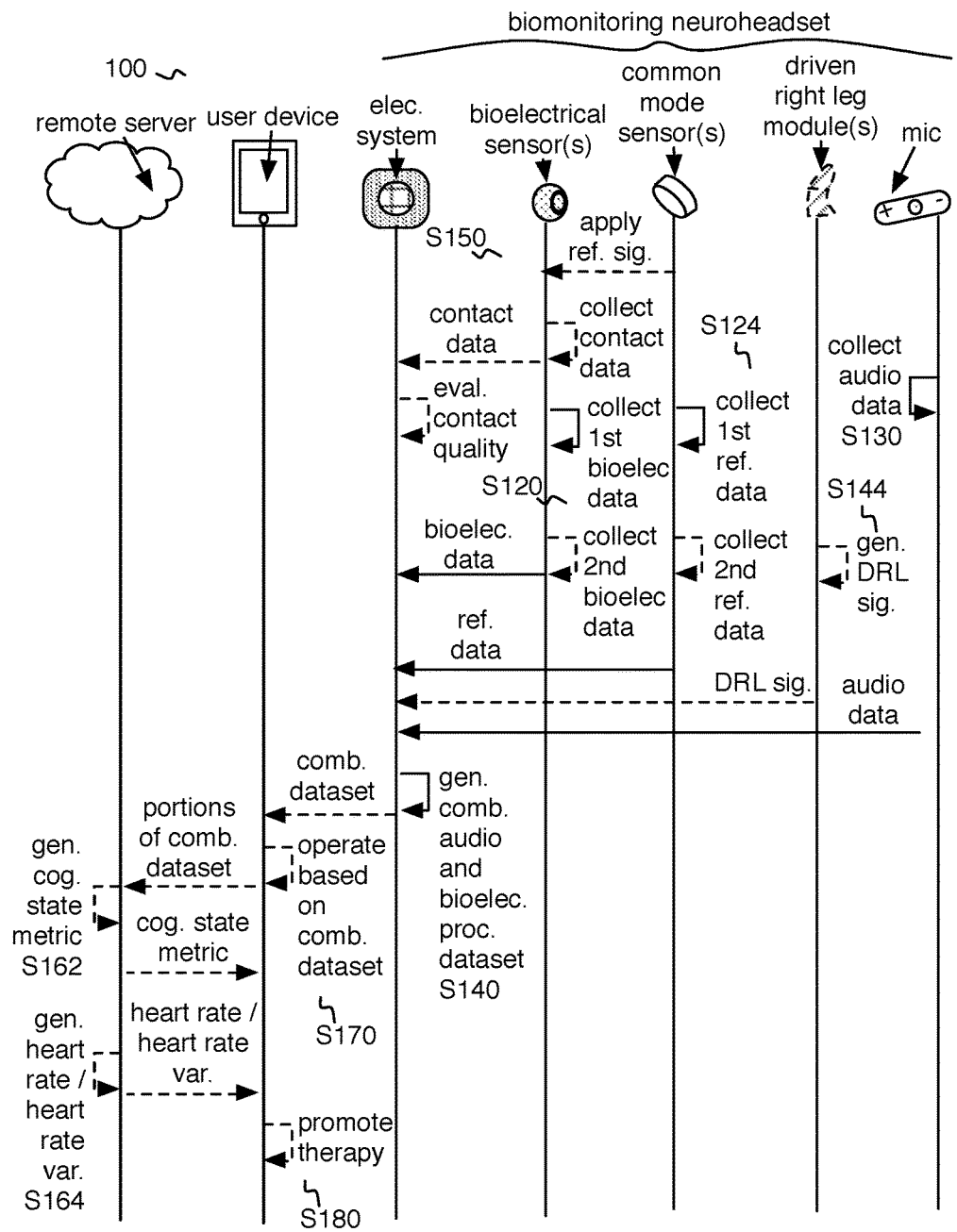
FIGS. 1-2 depict application flows of embodiments of a method for detecting bioelectrical and audios signal of a user.
Figure 2:
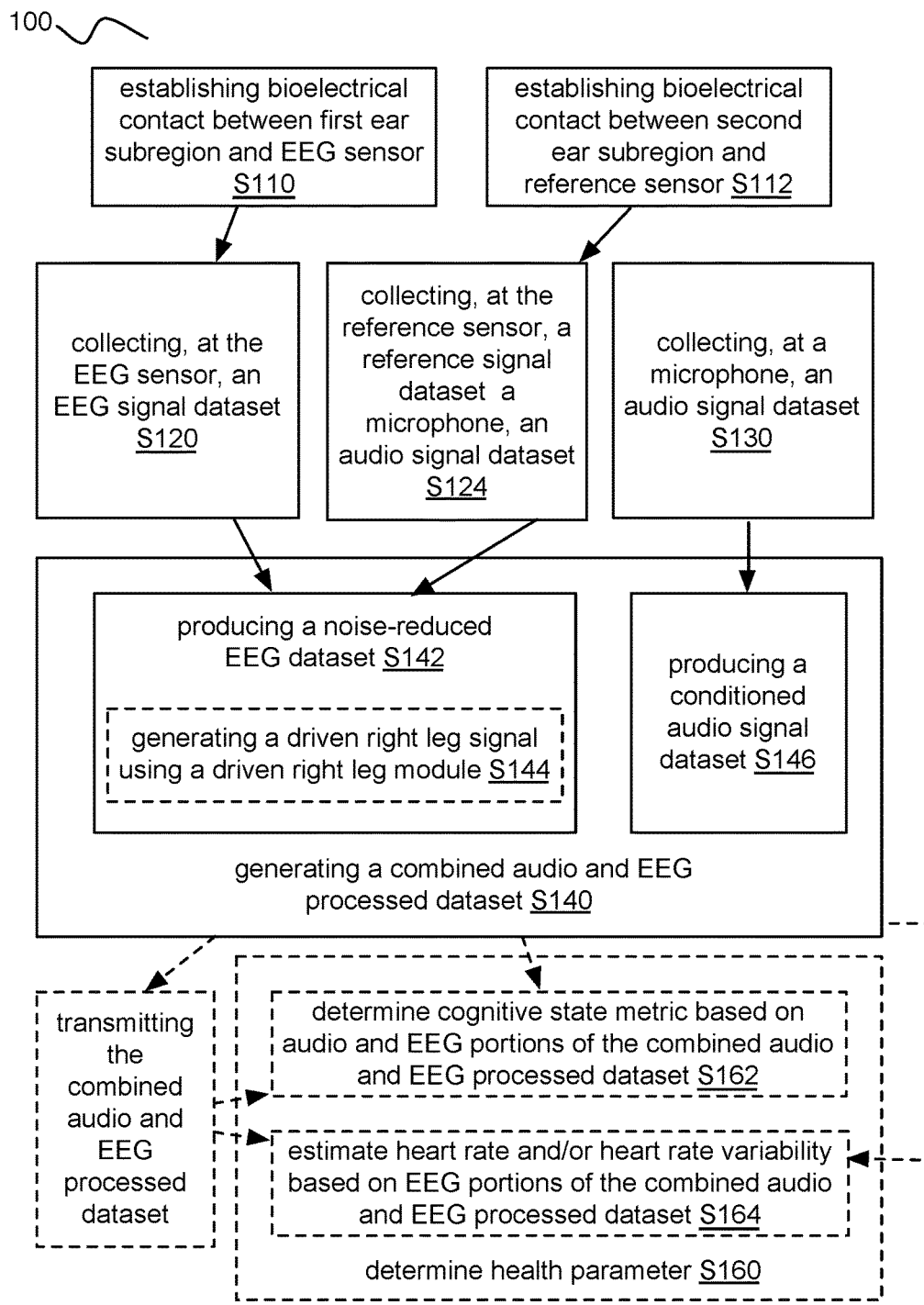

As shown in FIGS. 1-2, an embodiment of a method 100 for detecting bioelectrical signals and audio signals from a user, includes: establishing bioelectrical contact between a user and one or more sensors of a biomonitoring neuroheadset S110; collecting, at the one or more sensors, one or more bioelectrical signal datasets S120; collecting one or more reference signal datasets S124; collecting, at a microphone of the biomonitoring neuroheadset, an audio signal dataset S130; and generating a combined audio and bioelectrical signal processed dataset S140, including producing a noise-reduced bioelectrical signal dataset S142, and producing a conditioned audio signal dataset S146. While variations of the method can be performed exclusively by a biomonitoring neuroheadset, other variations of the method can involve performance of portions of the method by any component of a system 200, including one or more of a remote server, a local processing system, a user device (e.g., a smartphone, a laptop, a tablet, a desktop, a smartwatch, etc.), a third party device, and/or any other suitable component.

In variations, the method 100 functions to collect, process, and analyze bioelectrical signals with audio signals for monitoring psychological and/or physiological status of a user. The method 100 can additionally or alternatively function to leverage analyzed bioelectrical signals and audio signals to specify control instructions for a user device (e.g., a smartphone, a biomonitoring neuroheadset, etc.), to generate health parameters (e.g., a cognitive state metric describing emotional status, cardiovascular health parameters, etc.) describing a user, and/or to provide audio samples (e.g., audio therapy) at a speaker 260 of the biomonitoring neuroheadset. The method 100 is preferably performed with an embodiment, variation, or example of the system 200 (e.g., described in Section 4), but can alternatively be performed with any other suitable system and/or component.

Figure 4A:
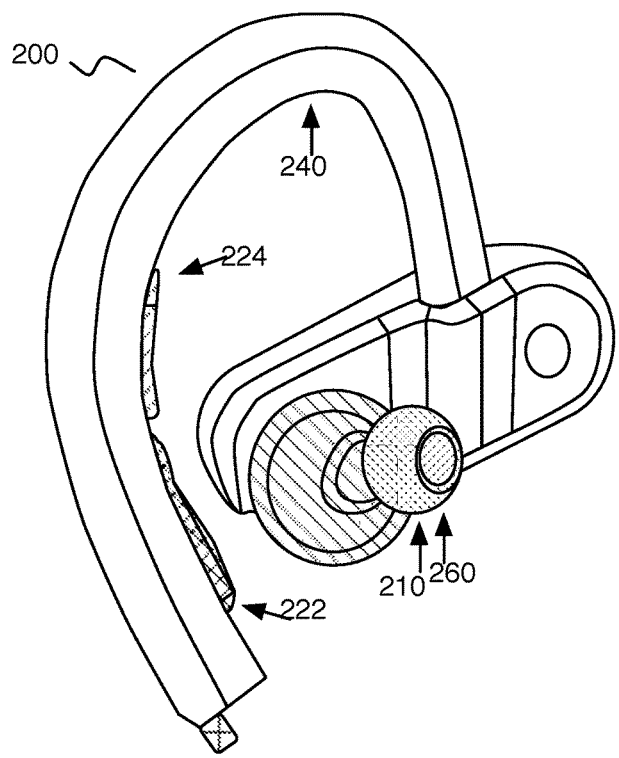
FIGS. 4A-4B depict variations of an embodiment of a system for detecting bioelectrical and audio signals of a user.
Figure 4B:
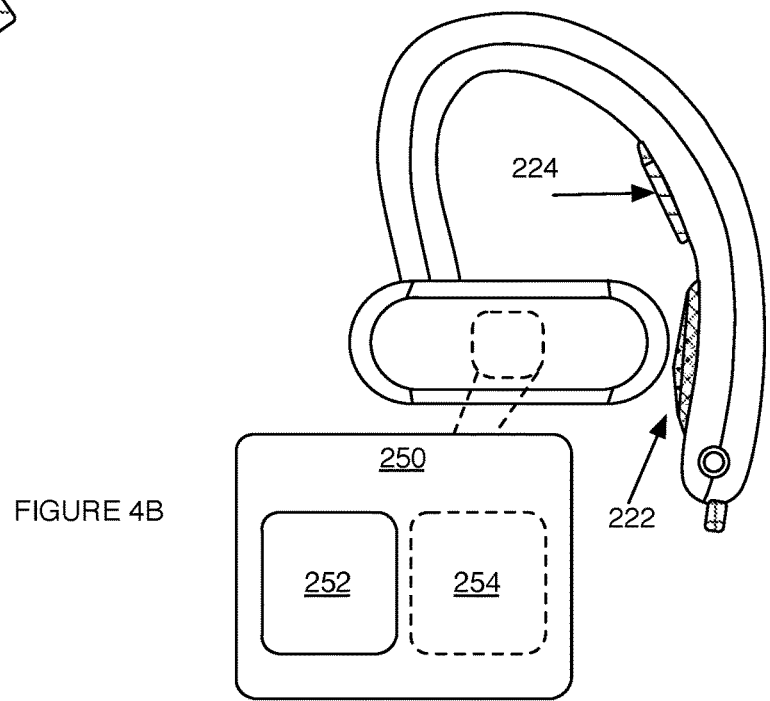

As shown in FIGS. 4A-4B, an embodiment of a system 200 for detecting bioelectrical signals from a user includes: one or more bioelectrical signal sensors 210 configured to collect bioelectrical signal data from the user; a noise reduction subsystem 220 including one or more reference sensors configured to collect reference signal data contemporaneously with the collection of bioelectrical signal data; a microphone 230 configured to collect an audio signal dataset from the user contemporaneously with the collection of the first bioelectrical signal dataset and the reference signal dataset; a wearable support frame 240 worn at a head region of the user, the wearable support frame 240 supporting and physically connecting the one or more bioelectrical sensors 210 and the one or more reference sensors; and an electronics subsystem 250 including a processing module 252 configured to produce a noise-reduced bioelectrical dataset from processing the bioelectrical signal data with the reference signal data, and to produce a conditioned audio signal dataset from processing the audio signal dataset for transmission with the noise-reduced bioelectrical signal dataset, the electronics subsystem 250 electronically connected to the one or more bioelectrical signal sensors 210, the noise reduction subsystem 220, and the microphone 230.

The system 200 functions to collect and process multiple types of data (e.g., electroencephalogram data, audio signal data, etc.) for monitoring psychological and/or physiological status of a user. The system 200 can additionally or alternatively function to ensure a high level of contact quality between sensors of the biomonitoring neuroheadset and the user, in order to accurately collect and analyze different types of data. The system 200 can perform any portions of the method 100 (e.g., described in Section 3), but the system 200 can additionally or alternatively perform any other suitable operations.

2. Benefits.

In specific examples, the method 100 and/or system 200 can confer several benefits over conventional methodologies for collecting and processing bioelectrical signals with audio signals. Traditional approaches can face limitations from inability to contemporaneously measure bioelectrical signals with audio signals while preventing cross-talk and sufficiently eliminating associated noise. However, in specific examples, the method 100 and/or system 200 can perform one or more of the following:

First, the technology can leverage a biomonitoring neuroheadset for continuously monitoring bioelectrical and audio signals of users for use in a plethora of time-dependent applications such as monitoring health status and neuromarketing. In an example of determining health parameters, the technology can analyze electroencephalogram (EEG) signals and user audio input in order to determine both psychological status (e.g., generating a cognitive state metric corresponding to a user's emotional state at a given time period) and physiological status (e.g., determining cardiovascular health parameters for a time period from EEG data collected proximal an ear region of the user). In an example of neuromarketing, the technology can collect EEG signals and audio commentary from a user as the user is exposed to different types of media (e.g., advertisements, television, movies, video games, etc.) in order to determine how different aspects of media effect a user's emotional state.

Second, the technology can simultaneously collect both bioelectrical signals (e.g., EEG, electrocardiogram, electromyography, electrooculography, etc.) and audio signals while preventing cross-talk and reducing noise associated with the signals in real-time. As such, the technology can generate combined bioelectrical signal and audio signal processed datasets that are accurate and primed for subsequent transmission (e.g., to a user device, to a remote processing module, etc.) and analysis (e.g., for evaluating cognitive state).

Third, the technology can optionally include speakers (e.g., embedded in an ear bud with an EEG sensor), which can be used for emitting audio samples (e.g., audio therapies generated based on evaluated cognitive state of a user). A user's response (e.g., EEG signal response, audio signal response, etc.) to emitted audio samples can be continuously monitored using the biomonitoring neuroheadset providing the audio sample.

Fourth, as the technology can collect bioelectrical signals and audio signals contemporaneously in real-time, generated analyses (e.g., generated health parameters, therapies, etc.) of collected data can be presented and/or promoted to a user in real-time (e.g., during the time period in which the data was collected). As such, the technology can provide real-time and/or retrospective (e.g., leveraging collected data stored at remote server) analyses.

The technology can, however, provide any other suitable benefit(s) in the context of collecting bioelectrical signals and audio signals for evaluating user status.

3. Method.

As shown in FIGS. 1-2, an embodiment of a method 100 for detecting bioelectrical signals and audio signals from a user, includes: establishing bioelectrical contact between a user and one or more sensors of a biomonitoring neuroheadset S110; collecting, at the one or more sensors, one or more bioelectrical signal datasets S120; collecting one or more reference signal datasets S124; collecting, at a microphone of the biomonitoring neuroheadset, an audio signal dataset S130; and generating a combined audio and bioelectrical signal processed dataset S140, including producing a noise-reduced bioelectrical signal dataset S142, and producing a conditioned audio signal dataset S146.

In some variations, the method 100 can additionally or alternatively include generating a driven right leg signal S144, monitoring contact quality of the at least one or more sensors S150, determining a health parameter based on the combined audio and bioelectrical signal processed dataset S160, controlling operation of a user device based on the combined audio and bioelectrical signal processed dataset S170, and/or emitting, at a speaker of the biomonitoring neuroheadset, an audio sample S180.

3.1 Establishing Bioelectrical Contact.

As shown in FIG. 2, Block S110 recites: establishing bioelectrical contact between a user and one or more sensors of a biomonitoring neuroheadset, which functions to facilitate a bioelectrical interface between an individual and a biosignal detector. Establishing bioelectrical contact S110 is preferably between one or more sensors of a biomonitoring neuroheadset and a human, but can additionally or alternatively be with a biomonitoring neuroheadset and any other suitable organism (e.g., a pet, an animal, etc.). One or more bioelectrical sensors of the biomonitoring neuroheadset preferably include one or more EEG sensors and one or more reference sensors (e.g., common mode sensor, sensors associated with a driven right leg module, etc.). Alternatively, the biomonitoring neuroheadset can omit reference sensors. However, the biomonitoring neuroheadset can additionally or alternatively include any bioelectrical signal sensors configured to detect any one or more of: electrooculography (EOG) signals, electromyography (EMG) signals, electrocardiography (ECG) signals, galvanic skin response (GSR) signals, magnetoencephalogram (MEG) signals, and/or any other suitable signal.

Relating to Block S110, bioelectrical contact is preferably established through sensors arranged at a particular location or region of the user (e.g., head region, torso region, etc.). For example, Block S110 can include establishing bioelectrical contact between a first subregion of an ear region of the user and an EEG sensor of a biomonitoring neuroheadset. In a specific example, the first subregion of the ear region (e.g., an ear region of a left ear) can include an ear canal (e.g., a left ear canal) of the user. In a variation of Block S110 where the biomonitoring neuroheadset includes a set of EEG sensors, Block S110 can include establishing bioelectrical contact between a first contralateral subregion of a contralateral ear region (e.g., an ear region of a right ear) of the user and a second EEG sensor of the biomonitoring neuroheadset, where the first contralateral subregion can include a contralateral ear canal (e.g., a right ear canal) of the user.

In another variation of Block S110 where the biomonitoring neuroheadset includes one or more common mode sensors Block S110 can additionally or alternatively include establishing bioelectrical contact between a second subregion of the ear region of the user and a common mode sensor of a noise reduction subsystem of the biomonitoring neuroheadset S112. In a specific example of the variation, the second ear subregion is proximal the first subregion, and the EEG sensor is proximal the common mode sensor. In another specific example, Block S112 can include establishing bioelectrical contact between a second contralateral subregion of the contralateral ear region of the user and a second common mode sensor of a noise reduction subsystem of the biomonitoring neuroheadset, where the first contralateral subregion is proximal the second contralateral subregion, and where the second EEG sensor is proximal the second common mode sensor. In this specific example, the second subregion can include an ear subregion proximal a mastoid process of a temporal bone of the user, and where the second contralateral subregion can include a contralateral ear subregion proximal a contralateral mastoid process of a contralateral temporal bone of the user.

In another variation of Block S110 where the biomonitoring neuroheadset includes one or more driven right leg (DRL) sensors of a driven right leg module, Block S110 can include establishing bioelectrical contact between a third subregion of the ear region of the user and a DRL sensor of a DRL module of the noise reduction subsystem S114. The third subregion is preferably at an ear region (e.g., proximal a mastoid process of a temporal bone of the user), but can alternatively be at any suitable anatomical position of the user.

In variations of Block S110, establishing bioelectrical contact can include any elements analogous to those disclosed in U.S. patent application Ser. No. 13/903,861 filed 28 May 2013, U.S. patent application Ser. No. 14/447,326 filed 30 Jul. 2014, and U.S. patent application Ser. No. 15/058,622 filed 2 Mar. 2016, which are hereby incorporated in their entirety by this reference. However, establishing bioelectrical contact between body regions of a user and different types of sensors can be performed in any suitable manner.

3.2 Collecting a Bioelectrical Signal Dataset.

As shown in FIGS. 1-2, Block S120 recites: collecting, at one or more sensors, one or more bioelectrical signal datasets, which functions to collect data indicative of a psychological and/or physiological state of a user. The collected dataset(s) preferably include bioelectrical signal data collected at one or more sensors in bioelectrical contact with the user as in Block S110. For example, Block S120 can include collecting one or more EEG, EOG, EMG, ECG, GSR, and/or MEG signal datasets at corresponding bioelectrical sensors. Additionally or alternatively, any suitable dataset (e.g., supplemental data, etc.) can be collected at a user device. Further, any number, size and/or size of datasets can be collected.

In relation to Block S120, collecting one or more bioelectrical signal datasets is preferably characterized by collection instructions given by a processing module (e.g., a control printed circuit board) of an electronics subsystem of the biomonitoring neuroheadset. Additionally or alternatively, Block S120 can include collecting one or more bioelectrical signal datasets according to predetermined (e.g., by a manufacturer, by a user, by a care provider, etc.) and/or automatically determined (e.g., based on a computational model, thresholds, etc.) collection instructions and/or parameters. However, collecting one or more bioelectrical signal datasets can be characterized by any suitable criteria.

With respect to temporal aspects relating to Block S120, collecting one or more bioelectrical signal datasets can be performed during, associated with, and/or correspond to any suitable temporal indicator (e.g., time point, time window, time period, duration, etc.). Time periods can be of any suitable length (e.g., on the order of seconds, minutes, hours, days, etc.). In a specific example, Block S120 can include collecting, at an EEG sensor, an EEG signal dataset from the user during a first time period. Additionally or alternatively, collecting one or more bioelectrical signal datasets S120 can be performed during time periods in which the user is performing a specific activity. Specific activities can include any combination of: engaging in content (e.g., digital content, television, music, film, video games, etc.), interacting with other individuals (e.g., during conversation, at a social activity, at a workplace activity), daily activities (e.g., at home, at work, during sleep, during meals, etc.), and/or any other suitable activity. However, collecting one or more bioelectrical signal datasets can be performed at any suitable time as the user performs any suitable action.

Regarding Block S120, additionally or alternatively, collecting one or more bioelectrical signal datasets can include any elements disclosed in U.S. patent application Ser. No. 13/903,861 filed 28 May 2013, U.S. patent application Ser. No. 14/447,326 filed 30 Jul. 2014, and U.S. patent application Ser. No. 15/058,622 filed 2 Mar. 2016, which are hereby incorporated in their entirety by this reference. However, Block S120 can be performed in any suitable manner.

3.3 Collecting a Reference Signal Dataset.

As shown in FIGS. 1-2, Block S124 recites: collecting one or more reference signal datasets, which functions to collect reference signal data for reducing noise associated with bioelectrical signal datasets collected in Block S120. Collecting one or more reference signal datasets is preferably performed at one or more common mode sensors with one or more DRL modules. In a specific example, Block S124 can include collecting, at a common mode sensor, a common mode signal dataset, where the common mode signal dataset can enable detection and removal of common-mode components of noise to facilitate downstream signal processing. Additionally or alternatively, one more collected reference signal datasets can include any suitable amount, type and/or combination of reference signals for reducing noise associated with any suitable dataset related to the method 100.

With respect to temporal aspects relating to Block S124, collecting one or more reference signal datasets is preferably performed in parallel, simultaneously, and/or contemporaneously with collecting one or more bioelectrical signal datasets as in Block S120. As such, Block S124 is preferably performed during the same temporal indicator (e.g., during the same time period) at which Block S120 is performed. In a specific example, Block S124 can include collecting, at a common mode sensor, a common mode signal dataset contemporaneously with collecting an EEG signal dataset during a time period. Additionally or alternatively, reference signal datasets can be collected in serial, before, after, and/or with any other suitable relationship to other portions of the method 100.

In a variation of Block S124, collecting reference signal datasets can include collecting a plurality of reference signal datasets at a set of a reference sensors of the biomonitoring neuroheadset. For example, the biomonitoring neuroheadset can include a set of two common mode sensors (e.g., a first common mode sensor proximal a left ear region, and a second common mode sensor proximal a right ear region). In this example, Block S124 can include collecting a first common mode signal dataset at the first common mode sensor, and collecting a second common mode signal dataset at the second common mode sensor. In another example, the biomonitoring neuroheadset can additionally or alternatively include a DRL module including a set of DRL sensors (e.g., a first DRL sensor proximal a first common mode sensor and a left ear region, and a second DRL sensor proximal a second common mode sensor and a right ear region). In examples with a plurality of reference sensors, reference signal datasets can be collected with the plurality of reference sensors contemporaneously, simultaneously, serially, and/or with any suitable temporal relationship.

Block S124 can additionally or alternatively include any elements disclosed in U.S. patent application Ser. No. 14/447,326 filed 30 Jul. 2014, which is hereby incorporated in its entirety by this reference. However, Block S124 can be performed in any suitable manner.

3.4 Collecting an Audio Signal Dataset.

As shown in FIGS. 1-2, Block S130 recites: collecting, at a microphone of the biomonitoring neuroheadset, an audio signal dataset, which functions to collect audio inputs from the user for use in determining a psychological and/or physiological state of the user. Additionally or alternatively, Block S130 can function to collect audio instructions from the user for controlling operation of a user device (e.g., a mobile computing device, a medical device, the biomonitoring neuroheadset, etc.). A collected audio signal dataset can data describing a user's speech, phonetic segments, prosody, intonation, tone, stress, rhythm, pitch, length, volume, timbre, frequency, intensity, breathing, breathing patterns, emotional state, form of utterance (e.g., statement, question, command, etc.) environmental noise (e.g., noise from a user's surroundings, from a nearby media device, etc., supplemental user noise (e.g., noise originating from lip movement, teeth movement, eating, etc.), noise from other users (e.g., speech from a conversation partner of the user, etc.), and/or any other suitable audio data.

Regarding Block S130, collecting an audio signal dataset is preferably performed one or more microphones of a biomonitoring neuroheadset, but can additionally or alternatively be performed at a different user device (e.g., at a audio recording application executing on a mobile computing device associated with the user, etc.), and/or any other suitable component.

In relation to temporal aspects relevant to Block S130, collecting an audio signal dataset is preferably performed in parallel, simultaneously, and/or contemporaneously with collecting one or more bioelectrical signal datasets as in Block S120 and/or collecting one or more reference signal datasets as in Block S124. In a specific example, Block S130 can include collecting, at a microphone of the biomonitoring neuroheadset, an audio signal from the user contemporaneously with collecting an EEG signal dataset and a common mode signal dataset during a time period. Additionally or alternatively, Block S130 can be performed before, after, in serial, and/or with any suitable temporal relationship relative other portions of the method 100. In variations, audio signals can be collected based on volume criteria (e.g., volume thresholds), content criteria (e.g., specific types of audio detected), processing module instructions, user selection (e.g., a user manually triggering a microphone to record audio input), and/or any other suitable criteria associated with audio inputs. For example, collecting an audio signal can include: detecting a noise volume of audio inputs at the microphone, and in response to the detected noise volume exceeding a threshold, collecting an audio signal dataset with the microphone. In this example, the volume threshold can be user-determined, manufacturer-determined, automatically determined (e.g., adjusted based on the volume of ambient environmental noise, based on GPS location, based on time of day, etc.), and/or determined in any other suitable manner. However, collecting an audio signal dataset can be performed at any suitable time based on any suitable criteria.

Block S130 can additionally or alternatively include any elements disclosed in U.S. patent application Ser. No. 13/903,832 filed 28 May 2013, which is hereby incorporated in its entirety by this reference. However, Block S130 can be performed in any suitable manner.

3.5 Generating a Combined Bioelectrical Signal and Audio Signal Dataset.

As shown in FIGS. 1-2, Block S140 recites: generating a combined audio and bioelectrical signal processed dataset, which functions to process audio and bioelectrical signal datasets, thereby generating a combined dataset for downstream analysis. As shown in FIG. 2, Block S140 can additionally or alternatively include producing a noise-reduced EEG dataset S142, generating a driven right leg signal using a driven right leg module S144, and/or producing a conditioned audio signal dataset S 144. Generating a combined audio and bioelectrical signal processed dataset can include performing one or more processing operations on one or more bioelectrical signal datasets (e.g., EEG signal datasets) collected as in Block S120, reference signal datasets (e.g., common mode signal datasets) collected as in Block S124, and/or audio signal datasets collected as in Block S130, but processing operations can be performed on any suitable dataset or combination of datasets. Processing operations can include: multiplexing, demultiplexing, combination of values (e.g., averaging values, etc.), compression, conversion (e.g., digital-to-analog conversion, analog-to-digital conversion), wave modulation (e.g., amplitude modifications, frequency modifications, phase modifications), normalization, filtering, noise reduction, smoothing, model fitting, transformations, mathematical operations (e.g., derivatives, moving averages, etc.), and/or any other suitable.

In a specific example, Block S140 can include multiplexing a noise-reduced EEG dataset (e.g., a common noise-reduced EEG dataset) and a conditioned audio signal dataset (e.g., processed into a form suitable for multiplexing), wherein the combined audio and EEG processed dataset is generated from the multiplexed common noise-reduced EEG dataset and the conditioned audio signal dataset. In this specific example, the method 100 can additionally include transmitting the combined audio and EEG processed dataset to a mobile computing device of the user; and demultiplexing, at a software component executing on the mobile computing device, the combined audio and EEG processed dataset. Processing operations can be performed on datasets in the digital signal domain, analog signal domain, and/or any other suitable form. Processing operations performed in generating a combined audio and bioelectrical signal processed dataset preferably enable isolation from electrical mains interference and/or protects against high frequency common mode signals (e.g., at-risk of being aliased into the EEG spectrum). However, any suitable processing operation can be performed on a dataset.

In relation to Block S140, generating a combined audio and bioelectrical signal processed dataset is preferably based on, determined by, and/or derived from a noise-reduced bioelectrical signal dataset and a conditioned audio signal dataset, but values from any suitable dataset can be used in generating a combined audio and bioelectrical signal processed dataset.

Regarding Block S140, any portion of generating a combined bioelectrical signal and audio signal processed dataset can be performed by a processing module of a biomonitoring neuroheadset, by a remote server, by a user device, and/or any other suitable device.

In relation to temporal aspects of Block S140, generating a combined bioelectrical signal and audio signal processed dataset is preferably performed in response to collecting an audio signal dataset contemporaneously with collecting a bioelectrical signal dataset and a reference signal dataset during a time period. Additionally or alternatively, combined bioelectrical signal and audio signal datasets can be generated without collection of a reference signal dataset. However, Block S140 can be performed based on any suitable criteria, including data characteristics (e.g., amount of collected data, types of collected data, data values, data requirements for transmission, etc.), biomonitoring neuroheadset status (e.g., battery state of charge, communication links established with other devices), status of other user devices, etc.), user initiation (e.g., a manual user request for cognitive state status, an audio signal request, an API request, etc.). Constituent datasets used in generating a combined bioelectrical signal and audio signal processed dataset are preferably associated with the same temporal indicator (e.g., collected during the same time period) and/or overlapping temporal indicators (e.g., collected during two different time periods with overlapping portions of time), but can additionally or alternatively be associated with non-overlapping temporal indicators, and/or any suitable temporal indicator. In a specific example, generating a combined bioelectrical signal and audio signal dataset includes generating the combined dataset from a bioelectrical signal dataset and a reference signal dataset, each dataset collected during a same time period.

3.5.A Producing a Noise-Reduced Bioelectrical Signal Dataset

As shown in FIG. 2, Block S140 can additionally or alternatively include Block S142, which recites: producing one or more noise-reduced bioelectrical signal datasets. Block S142 functions to process a bioelectrical signal dataset (e.g., an EEG signal dataset collected as in Block S120) with a reference signal dataset (e.g., a common mode signal dataset collected as in Block S124) in order to remove noise from one or more bioelectrical signal datasets. Producing one or more noise-reduced bioelectrical signal datasets preferably includes producing a noise-reduced EEG signal dataset. For example, Block S142 can include producing a common noise-reduced EEG dataset from the first EEG signal dataset and the first common mode signal dataset. However, a noise-reduced version of any suitable bioelectrical signal dataset and/or other dataset can be generated.

Regarding Block S142, producing one or more noise-reduced bioelectrical signal dataset preferably includes using one or more reference signals to filter, subtract, and/or otherwise eliminate noise present in one or more bioelectrical signal datasets. For example, producing a noise-reduced bioelectrical signal dataset can include reducing common mode noise (e.g., noise conducted on lines in the same direction). Additionally or alternatively, Block S142 can include reducing differential mode noise (e.g., conducted on lines characterized by opposite directions), random noise, coherent noise, and/or any other suitable type of noise. However, reference signal datasets can be used in any suitable manner for reducing noise.

In a variation of Block S142, a plurality of reference signal datasets collected by a set of reference signal sensors can be used in producing a noise-reduced bioelectrical signal dataset. Block S142 can include processing a plurality of reference signal datasets into a single combined reference signal dataset. Processing operations preferably include averaging operations (e.g., averaging values from multiple reference signal datasets collected during a same time period), but can include any of the processing operations described with respect to Block S140, and/or any other suitable processing operation. In a specific example, generating a combined (e.g., averaged) common mode signal dataset includes performing an averaging operation with a first common mode signal dataset (e.g., collected at a left ear region of the user during a time period) and a second common mode signal dataset (e.g., collected at a right ear region of the user during the time period), and where producing a common noise-reduced EEG dataset comprises producing the common noise-reduced EEG dataset from the combined common mode signal dataset. However, utilizing a set of reference signal datasets collected by a set of reference signal sensors can be performed in any suitable manner for generating a noise-reduced bioelectrical signal dataset.

3.5.B. Generating a Driven Right Leg Signal.

As shown in FIG. 2, Block S140 can additionally or alternatively include Block S144, which recites: generating a driven right leg signal. Block S144 functions to reduce common mode interference (e.g., from electromagnetic interference) in generating a common mode noise-reduced dataset for downstream analysis. Generating a driven right leg signal preferably includes actively canceling common mode interference with a driven right leg module of a noise reduction subsystem of the biomonitoring neuroheadset. The driven right leg module is preferably characterized by a feedback reference location at a third subregion of the ear region (e.g., where a bioelectrical signal sensor is positioned proximal a first subregion, and where a reference signal sensor is positioned proximal a second subregion), where producing the noise-reduced bioelectrical signal dataset includes producing the noise-reduced bioelectrical signal dataset from the driven right leg signal. The third subregion is preferably at an ear region of the user, but can alternatively be at any suitable anatomical position of the user. In a specific example, the third subregion includes the mastoid process of the temporal bone corresponding to the ear region, but can include any other suitable region of the ear. Additionally or alternatively, a driven right leg module can reduce common mode noise in any suitable manner.

In relation to temporal aspects of Block S144, generating a driven right leg signal is preferably performed contemporaneously with collecting a common mode signal dataset (e.g., as in Block S124), such that common mode interference can be canceled by the driven right leg module during the time period in which the bioelectrical signal dataset and corresponding mode signal dataset are collected. However, generating a driven right leg signal can be performed at any suitable time.

In a variation of Block S144, generating one or more driven right leg signals can be performed by one or more driven right leg modules including a plurality of feedback reference locations. Feedback reference locations beyond the first are preferably redundant, such that sufficient contact between the driven right leg module and the user is only required for a single feedback reference location in order to facilitate common mode interference reduction. Additionally or alternatively, driven right leg module functionality can be allocated across feedback reference locations, such that additional noise reduction can be conferred through sufficient contact between a user and multiple feedback reference locations. In a specific example, the driven right leg module can be characterized by a first feedback reference location at a third subregion of an ear region (e.g., where a first bioelectrical signal sensor is positioned at a first subregion, and a first common mode sensor is positioned at a second subregion), by a second feedback reference location at a third contralateral subregion (e.g., where a second bioelectrical signal sensor is positioned at a first contralateral subregion, and a second common mode sensor is positioned at a second contralateral subregion) of the contralateral ear region, where the third contralateral subregion is proximal the first and the second contralateral subregions of the contralateral ear region, and where generating the driven right leg signal is in response to adequate contact between the user and the driven right leg module at least at one of the first feedback reference location and the second feedback reference location. However, this variation of Block S144 can be performed in any suitable manner.

Additionally or alternatively, Block S140, S142, and/or S144 can include any elements described in U.S. patent application Ser. No. 14/447,326 filed 30 Jul. 2014, which is herein incorporated in its entirety by this reference. However, Block S144 can be performed in any suitable manner.

3.5.C Producing a Conditioned Audio Signal Dataset.

As shown in FIG. 2, Block S140 can additionally or alternatively include Block S146, which recites: producing a conditioned audio signal dataset. Block S146 functions to process the audio signal into a condition suitable for transmission with a bioelectrical signal dataset and/or a noise-reduced bioelectrical signal dataset. Producing a conditioned audio signal dataset can include applying one or more processing operations to one or more audio signal datasets (e.g., collected as in Block S130), where the processing operations can include one or more processing operations described in relation to Block S140, audio signal processing approaches (e.g., equalization, pitch shift, time stretching, resonation, synthesizers, modulation, filtering, phaser, flanger, echo, etc.), and/or any other suitable processing operation. In a specific example, producing a conditioned audio signal dataset can be determined from, generated by, and/or derived from processing the audio signal dataset for transmission with the common noise-reduced EEG dataset. In another specific example, producing a conditioned audio signal dataset includes transforming the audio signal dataset into a form suitable for multiplexing with a bioelectrical signal dataset and/or noise-reduced bioelectrical signal dataset. However, conditioned audio signal datasets can be produced from any suitable constituents as a result of any suitable processing operations.

In relation to temporal aspects of Block S146, producing a conditioned audio signal dataset can be performed with any suitable temporal relationship (e.g., contemporaneously, in parallel with, serially, in response to, before, after, etc.) in relation to Blocks S140, S142, S144, and/or any other suitable portion of the method 100. However, producing a conditioned audio signal dataset can be performed in any suitable manner.

3.6 Monitoring Contact Quality.

As shown in FIG. 1, the method 100 can additionally or alternatively include Block S150, which recites: monitoring contact quality of the at least one or more sensors. Block S150 functions to facilitate high quality sensor signals through adequate coupling between the user and one or more sensors of a biomonitoring neuroheadset. Contact quality is preferably monitored for one or more bioelectrical signal sensors (e.g., contact quality between an EEG sensor and an ear canal region) and/or reference signal sensors (e.g., contact quality between a common mode sensor and an ear region proximal the temporal bone; contact quality between a DRL sensor and an ear region proximal the temporal bone, etc.). However, monitoring contact quality can be performed for any suitable sensor. Monitoring contact quality is preferably performed for a sensor with a target position proximal an ear region of a user, but can additionally or alternatively be performed for sensors with target positions at any suitable anatomical position of a user. However, monitoring contact quality can be performed for any suitable sensor at any suitable location.

With respect to temporal aspects relating to Block S150, contact quality is preferably continuously monitored, in order to facilitate immediate real-time feedback to a user in response to detection of an uncoupling state between one or more sensors and the user. Monitoring contact quality S150 can additionally or alternatively be associated with and/or performed during a temporal indicator (e.g., a time period prior to collection of a bioelectrical signal dataset as in Block S120), but can otherwise be performed at any suitable time in relation to other portions of the method and/or at any appropriate time.

In a variation, Block S150 can include applying a reference signal with one or more sensors. In this variation, a reference signal preferably characterized by low voltage and low current can be applied to the user by one or more sensors (e.g., one or more electrodes of the biomonitoring neuroheadset). The reference signal can be a square wave, a sine wave, another suitable waveform, an impedance measure, and/or any other applicable reference signal. However, the reference signal can possess any suitable properties.

In relation to this variation of Block S150, one or more reference signals are preferably applied by one or more reference signal sensors (e.g., a common mode sensor, a DRL sensor of a DRL module, etc.), but can otherwise be applied by any suitable sensor. In examples where a DRL sensor applies a reference signal, the reference signal can be combined with a biasing signal and injected through a DRL electrode positioned at a feedback reference point of the DRL module. However, sensors applying reference signals can be characterized by any suitable trait.

In another variation of Block S150, monitoring contact quality can additionally or alternatively include generating a contact quality metric. Generated contact quality metrics preferably indicate the quality of coupling between a sensor and a user for accurately collecting biosignals. Generated contact quality metrics can possess any suitable form, including numerical (e.g., probabilities of sufficient contact quality, raw values, processed values, etc.), verbal (e.g., verbal indications of contact quality, etc.), graphical (e.g., colors indicating level of contact quality, educational graphics for facilitating improved contact quality, etc.), and/or any suitable form. Generating a contact quality metric is preferably performed at a processing module of the biomonitoring neuroheadset, but can additionally or alternatively be performed at another user device, a remote server, and/or any suitable component. However, generating a contact quality metric can be otherwise performed.

In another variation of Block S150, monitoring contact quality can additionally or alternatively include notifying a user of contact quality. Notifying a user regarding contact quality preferably includes notifying a user in real-time regarding the contact quality for one or more sensors of the biomonitoring neuroheadset. Notifying a user can include providing a visual notification (e.g., a notification presented at a user interface of the biomonitoring neuroheadset, a push notification at a smartphone of a user, etc.), an auditory notification (e.g., sounds emitted through a speaker of the biomonitoring neuroheadset, etc.), a haptic notification (e.g., a vibration of the biomonitoring neuroheadset), and/or any other suitable type of notification. However, notifying a user of contact quality can be performed in any suitable manner.

In another variation of Block S150, monitoring contact quality can additionally or alternatively include automatically adjusting the biomonitoring neuroheadset to establish bioelectrical contact between one or more sensors and the user. Automatically adjusting the biomonitoring neuroheadset can include: directing the orientation of one or more sensors of the biomonitoring neuroheadset (e.g., automatically orienting one or more sensors towards a target anatomical position of the user), providing an actuating force (e.g., a vibration, a biasing force, etc.) to move one or more sensors into bioelectrical contact with the user, adjusting data collection parameters of one or more sensors, and/or any other suitable adjustments of the biomonitoring neuroheadset. Automatically adjusting the biomonitoring neuroheadset is preferably performed in response to detecting an unsuitable contact quality for collection of biosignals, but can additionally or alternatively be performed at any suitable time. However, automatically adjusting the biomonitoring neuroheadset can be performed in any suitable fashion.

Additionally or alternatively, Block S150 can include any elements described in U.S. patent application Ser. No. 12/270,739, filed 13 Nov. 2008, which is herein incorporated in its entirety by this reference. However, Block S150 can be performed in any suitable manner.

3.7 Determining a Health Parameter.

As shown in FIG. 2, the method 100 can additionally or alternatively include Block S160, which recites: determining one or more health parameters for a user based on the combined audio and bioelectrical signal processed dataset. Block S160 functions to analyze audio and/or bioelectrical signals in determining a parameter describing physiological and/or psychological status of a user. Types of health parameters can include any one or more of: cognitive state metrics, cardiovascular parameters, diagnostic analyses (e.g., identification of symptoms correlated with a diagnosis, etc.), treatment response parameters (e.g., response to medication, response to therapy, etc.), communication disorders (e.g., expressive language disorder, language impairment, autism spectrum disorder, etc.), and/or any other suitable health parameter descriptive of a physiological and/or psychological status of a user.

In relation to Block S160, determining a health parameter is preferably based on, determined by, and/or derived from the combined audio and bioelectrical signal processed dataset (e.g., based on both audio signals and bioelectrical signals collected by sensors and/or a microphone of a biomonitoring neuroheadset). For example, determining a health parameter can include extracting audio features from audio signals associated with the combined audio and bioelectrical signal dataset; extracting bioelectrical features (e.g., EEG-related features) from bioelectrical signals (e.g., EEG signals) associated with the combined audio and bioelectrical signal dataset; processing the audio features and bioelectrical features with a health parameter model to determine one or more health parameters for the user. Additionally or alternatively, data associated with any suitable dataset can be used in generating a health parameter. In variations, determining one or more health parameters can include generating and/or implementing one or more health parameter models. Generating a health parameter model can include processing any combination of probabilities properties, heuristic properties, deterministic properties, and/or any other suitable feature algorithmically to determine health parameters of a user. In a specific example, Block S160 can include training a machine learning health parameter model based on audio features, bioelectrical signal features, and corresponding health parameter labels; predicting a health parameter for a user from using the trained machine learning health parameter model with user audio feature inputs and user bioelectrical signal feature inputs. Additionally or alternatively. Machine learning approaches can include any approaches described in Section 4, and/or any suitable machine learning approach. However, determining a health parameter can be performed with any suitable approach.

Regarding Block S160, determining a health parameter is preferably performed by a remote server, but portions of Block S160 can additionally or alternatively be performed by a biomonitoring neuroheadset, another user device (e.g., a user smartphone, a user computer, etc.), and/or any other suitable component. Determining a health parameter S160 is preferably performed after generating a combined audio signal and bioelectrical signal processed dataset as in Block S160. For example, Block S160 can be performed in response to receiving, at a remote server, audio signal data and bioelectrical signal data associated with the combined audio signal and bioelectrical signal processed dataset. Additionally or alternatively, determining a health parameter can be performed before generating a combined radio signal and bioelectrical signal processed dataset, or at any suitable time. Health parameters of different types can be generated contemporaneously, in parallel, in serial, and/or with any suitable time relationship. For example, the method 100 can include generating a cognitive state metric and a cardiovascular parameter for a user contemporaneously during a time period. However, portions of Block S160 can be performed by an suitable component at any suitable time.

In specific examples, Block S160 can additionally or alternatively include testing for perceptual and/or cognitive function. Examples of psychological and/or physiological functions that can be tested can include one or more of: deafness, low level brain function, mental disorders, sensor disorders, and/or any other suitable perceptual and/or cognitive function. Testing for perceptual and/or cognitive function preferably includes emitting an audio sample (e.g., as in Block S180) with one or more speakers of the biomonitoring neuroheadset; collecting bioelectrical signal data (e.g., with an EEG sensor) contemporaneously with emitting the audio sample; and generating a perceptual and/or cognitive function parameter describing the functionality of a psychological and/or physiological aspect of the user. Perceptual and/or cognitive function parameters can be generated based on multiple EEG datasets (e.g., where the data is averaged over the repeated acquisitions) collected contemporaneously with emission of a set of audio samples (e.g., a set of different audio samples, a set of the same audio sample repeated multiple times, etc.), but can additionally or alternatively be generated based on, determined by, and/or derived from any suitable data (e.g., supplemental sensor data, etc.). However, testing for perceptual and/or cognitive function can be performed in any suitable manner.

3.7.A Determining a Cognitive State Metric.

In a variation of Block S160, determining one or more health parameters can additionally or alternatively include determining one or more cognitive state metrics S162. A cognitive state metric preferably indicates a cognitive state of a user. Cognitive state can include one more of: mood, emotional state, psychological health, focus level, thought processes, language abilities, memories, reasoning abilities, and/or any suitable cognitive state. Determining a cognitive state is preferably based on, determined by, and/or derived from audio data and bioelectrical data associated with at least one of: raw datasets (e.g., collected bioelectrical signal datasets as in Block S120, collected audio signal datasets as in Block S130), processed datasets (e.g., noise-reduced bioelectrical signal datasets, conditioned audio signal datasets, combined audio signal and bioelectrical signal datasets, etc.), cardiovascular parameter data (e.g., heart rate and/or heart rate variability generated as in Block S164), and/or any other suitable data. In a specific example, Block S162 can include receiving, at a remote server, a common noise-reduced EEG signal portion and an audio signal portion of a combined audio and EEG processed dataset; and generating a cognitive state metric based on the common noise-reduced EEG signal portion and the audio signal portion, wherein the cognitive state metric indicates a cognitive state of the user during a time period (e.g., a time period in which the raw EEG dataset and raw audio signal dataset were collected). Additionally or alternatively, determining a cognitive state metric can include any elements described in U.S. application Ser. No. 13/903,832, filed 28 May 2013, and U.S. application Ser. No. 15/058,622 filed 2 Mar. 2016, each of which are herein incorporated in their entirety by this reference. However, determining a cognitive state metric can be performed in any suitable manner.

3.7.B Determining a Cardiovascular Parameter.

In another variation of Block S160, determining one or more health parameters can additionally or alternatively include determining one or more cardiovascular parameters S164. Cardiovascular parameters can include one or more of: heart rate, heart rate variability, blood pressure, blood pressure variability, blood flow, heartbeat signatures, measures of blood vessel stiffness, measures indicative of atherosclerosis or other cardiovascular disease, other measures of cardiovascular risk, and/or any other suitable cardiovascular parameter. Determining one or more cardiovascular parameters S164 is preferably based on, determined by, and/or derived from bioelectrical signal features associated with a bioelectrical signal dataset (e.g., collected as in Block S120), a noise-reduced signal dataset (e.g., generated as in Block S142), bioelectrical signal portions of a combined noise and bioelectrical signal processed dataset (e.g., generated as in Block S140), and/or any suitable datasets including bioelectrical signal features. Additionally or alternatively, determining one or more cardiovascular parameters S164 can be based on audio signal features (e.g., breathing patterns) extracted from datasets associated with Block S130, S140, S144, and/or any suitable dataset. However, any suitable cardiovascular parameters can be generated from any suitable data.

In a variation of Block S164, determining one or more cardiovascular parameters is preferably based on detecting a slow oscillation in collected EEG signals, the slow oscillation arising from blood flow in sync with a pulse of a user. Collected EEG signals (e.g., noise-reduced EEG signals of a combined audio and EEG processed dataset) also preferably include PQRST complex sequences (e.g., analogous to PQRST spike sequences observed in ECG signals). In a specific example, Block S164 can include identifying a blood flow time-varying oscillation in noise-reduced values of a noise-reduced EEG dataset (e.g., a common noise-reduced EEG dataset); and estimating at least one of a heart rate and a heart rate variability based on the blood flow time-varying oscillation in noise-reduced values, where the at least one of the heart rate and the heart rate variability corresponds to a time period (e.g., a time period in which the raw EEG dataset was collected). In this specific example, identifying the blood flow time-varying oscillation in noise-reduced values can include identifying a set of QRS complex sequences in the noise-reduced values of the noise-reduced EEG dataset, and where estimating the at least one of the heart rate and the heart rate variability is based on the set of QRS complex sequences. However, determining one or more cardiovascular parameters can be performed in any suitable manner.

Additionally or alternatively, Blocks S160, S162, and S164 can be performed in any suitable fashion.

3.8 Controlling Operation of a User Device.

Figure 3:
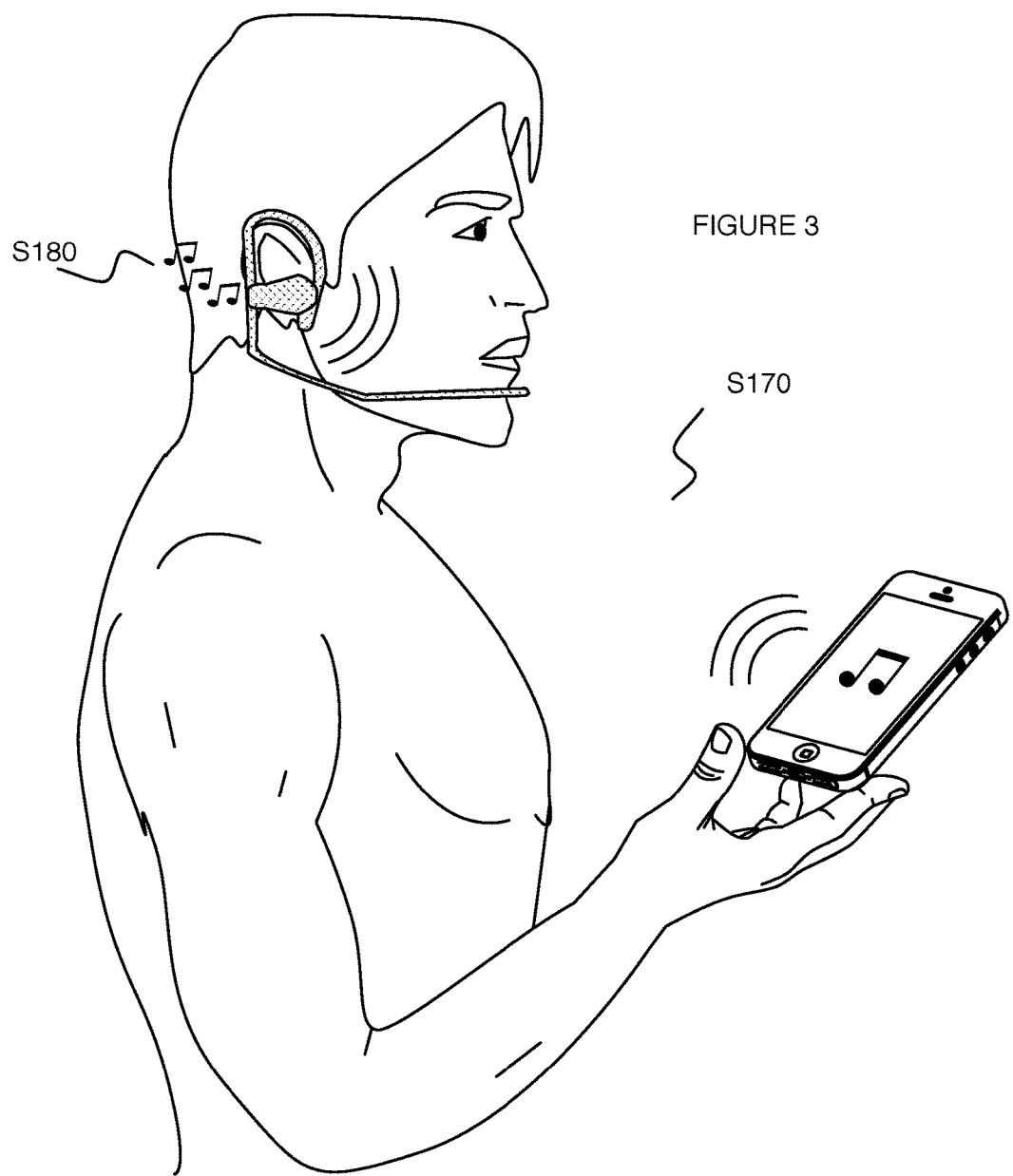
FIG. 3 depicts a schematic representation of an example of controlling a user device and emitting an audio sample.

As shown in FIGS. 1 and 3, the method 100 can additionally or alternatively include Block S170, which recites: controlling operation of a user device based on the combined audio and bioelectrical signal processed dataset. Block S170 functions to instruct a user device to perform one or more operations based on analysis of at least one of audio signal data and/or EEG signal data collected in association with the biomonitoring neuroheadset. Controllable user devices preferably include the biomonitoring neuroheadset, a user device (e.g., a mobile computing device, a computer, etc.) in communication (e.g., wired communication, wireless communication, etc.) with the biomonitoring neuroheadset, but can additionally or alternatively include a smart appliance (e.g., an internet-enabled television, video game console, cooking appliance, exercise device, etc.), and/or any other suitable device. In a specific example, the method 100 can include transmitting a combined audio and EEG processed dataset to a computing device of the user; generating, at a software component executing on the computing device, an analysis of an audio signal portion of the combined audio and EEG processed dataset; receiving, at the biomonitoring neuroheadset, operation instructions transmitted by the computing device and generated based on the analysis of the audio signal portion; and operating the biomonitoring neuroheadset based on the operation instructions.

Regarding Block S170, controllable operations for a user device can include: power operations (e.g., turning on/off, charging, battery modes, etc.), data collection operations (e.g., controlling a biomonitoring neuroheadset to collect bioelectrical signal datasets, reference signal datasets, audio signal datasets, etc.), controlling applications executable on the user device (e.g., controlling applications related to alarm, navigation, weather, timer, user-downloaded applications, calls, voicemail, location, email, schedule, entertainment, health & fitness, news, social, music, messaging, communication, etc.), transceiving operations (e.g., controlling a user device to transmit a dataset, configuring a user device to receive a dataset, etc.), and/or any other suitable operation associated with a user device. In a specific example, Block S170 can include controlling, with the microphone of the biomonitoring neuroheadset, operations associated with a mobile computing device (e.g., smart phone) of a user, including at least one of: phone calling features, web meeting features, voice recording (e.g., voice memo) features, virtual assistant features, voice-to-text features, and/or any other suitable features associated with a mobile computing device. However, any suitable operation can be controlled with respect to any suitable user device.

In relation to Block S170, controlling operation of a user device is preferably based on, determined by, and/or derived from analysis of audio and/or bioelectrical signal data associated with the combined audio and bioelectrical signal processed dataset, but can additionally or alternatively be associated with any suitable dataset. Regarding analysis of audio data for controlling operation of a user device, analyses can include: speech recognition approaches (e.g., using Hidden Markov models, machine learning models such as those described in Section 4, neural networks, dynamic time warping, etc.), audio signal processing (e.g., audio signal processing approaches described with respect to Block S146), and/or any other suitable analyses. Regarding analysis of bioelectrical signal data of controlling operation of a user device, analyses can include: bioelectrical signal processing (e.g., approaches described with respect to Block S140, S142, etc.), cognitive state metric analyses (e.g., as in Block S160), and/or any other suitable analyses for determining user intent based on bioelectrical signals. Additionally or alternatively, controlling operation of a user device can be based on any suitable data and/or approach. In a specific example, Block S170 can include: extracting audio features from audio signal data associated with the combined audio and bioelectrical signal dataset; extracting bioelectrical signal features from bioelectrical signal data associated with the combined audio and bioelectrical signal dataset; generating user device control instructions based on the extracted audio features and bioelectrical signal features; transmitting the control instructions to the user device (e.g., the user device for which the control instructions were generated), the control instructions configured to instruct operation of the user device.

However, controlling operation of a user device can be performed in any suitable manner.

3.9 Emitting an Audio Sample.

As shown in FIGS. 1 and 3, the method 100 can additionally or alternatively include Block S180, which recites:

emitting, at a speaker of the biomonitoring neuroheadset, an audio sample. Block S180 functions to output audio at one or more biomonitoring neuroheadset speakers to promote a therapy and/or facilitate physiological and/or psychological monitoring (e.g., a user response to the outputted audio) of the user. Emitting an audio sample can include emitting audio for any one or more of: promoting an audio therapy (e.g., a cognitive behavioral therapy audio session, etc.), monitoring a user response to the audio (e.g., monitoring a user response to an auditory component of media content that the user is engaging in, etc.), emitting an audio sample in response to user instruction (e.g., a user instructing for the emission of a particular song stored on the user's smartphone, etc.), and/or for any suitable purpose. Emitting an audio sample can additionally or alternatively include selecting an audio sample to emit based on audio data and/or bioelectrical signal data (e.g., EEG signal data) associated with a dataset described in Blocks S120, S124, S130, S140, S142, S144, S146, S162, and/or any suitable dataset. However, emitting an audio sample can be based on any suitable data.

In a variation of Block S180, emitting an audio sample can be based on a cognitive state metric generated as in Block S162. For example, Block S180 can include determining an audio therapy to modify the cognitive state of the user, based on the cognitive state metric; and promoting, at a speaker of the biomonitoring neuroheadset, the audio therapy to the user. In a specific example, emitting an audio sample can include, in response to generating a cognitive state metric indicating a negative emotional state of the user, emitting an audio sample characterized by audio features configured to invoke a positive emotional state of the user. However, emitting an audio sample based on a cognitive state metric can be performed in any suitable manner.

In another variation of Block S180, emitting an audio sample can additionally or alternatively include emitting an audio sample based on one or more cardiovascular parameters (e.g., generated as in Block S164). For example, emitting an audio sample can include selecting an audio sample based on matching an audio feature (e.g., beats per minute, music genre, types of instruments, vocals, date of publication, audio waveform features, etc.) with a cardiovascular feature one or more cardiovascular parameters. In a specific example, for a user engaging in physical activity (e.g., jogging), emitting an audio sample can include selecting a song with a beats per minute feature approximately matching a heart rate (e.g., an instantaneous heart rate, an average heart rate over a time period, etc.) of the user. In another example, an audio therapy can be selected and/or promoted based on a one or more cardiovascular features. For example, a soothing audio sample can be emitted at a speaker of a biomonitoring neuroheadset in response to generation of a cardiovascular parameter indicating a high cardiovascular risk (e.g., high blood pressure, increased heart rate, irregular heart rate, high heart rate variability, etc.). However, emitting an audio sample based on one or more cardiovascular parameters can be performed in any suitable fashion.

In another variation of Block S180, emitting an audio sample can based on data characterized by a plurality of data types (e.g., cardiovascular data, health parameters generated as in Block S160, cognitive state data, EEG data, etc.) For example, emitting an audio sample can include selecting an audio sample based on an analysis of one or more cognitive state metrics (e.g., generated as in Block S162) and one or more cardiovascular parameters (e.g., generated as Block S164). In a specific example, the method 100 can additionally or alternatively include generating a cognitive state metric based on EEG data associated with a combined audio and EEG dataset; generating a cardiovascular parameter based on the EEG data associated with the combined audio and EEG dataset; identifying one or more target health statuses (e.g., a psychological state, a physiological state) based on the cognitive state metric and the cardiovascular parameter; and emitting an audio sample configured to facilitate user achievement of the one or more target health statuses. In another specific example, the method 100 can include identifying a stressed user state based on a cognitive state metric (e.g., a metric indicating emotions of frustration) and a cardiovascular parameter (e.g., a high blood pressure); selecting an audio sample including audio features associated with a relaxed emotional state; and emitting the audio sample at one or more speakers of a biomonitoring neuroheadset. However, emitting an audio sample based on data typified by a plurality of data types can be performed in any suitable manner.

Regarding Block S180, in variations, Blocks S120, S124, S130, and/or other suitable portions of the method 100 can be performed contemporaneously with, in parallel with, serially, and/or in response to emitting an audio sample at a speaker of the biomonitoring neuroheadset S180. In a specific example, the method 100 can include, in response to promoting an audio therapy to the user at the speaker: collecting, at a first EEG sensor, a second EEG signal dataset (e.g., where the first EEG signal dataset was collected prior to emission of the audio therapy) from the user during a second time period (e.g., where the first time period corresponded to collection of the first EEG dataset); collecting, at the first common mode sensor, a second common mode signal dataset (e.g., where the first common mode signal dataset was collected during the first time period) contemporaneously with collecting the second EEG signal dataset during the second time period; collecting, at the microphone, a second audio signal dataset (e.g., where the first audio signal dataset was collected during the first time period) from the user contemporaneously with collecting the second EEG signal dataset and the second common mode signal dataset during the second time period; and generating a second combined audio and EEG processed dataset based on the second EEG signal dataset, the second common mode signal dataset, and the second audio signal; and generating a second cognitive state metric based on the second combined audio and EEG processed dataset, wherein the second cognitive state metric indicates a cognitive state response to the audio therapy during the second time period. However, Block S180 can have any suitable relationship with other portions of the method.

With respect to temporal aspects relating to Block S180, emitting an audio sample is preferably performable in real-time or near real-time. For example, emitting an audio sample can be performed during a time period in which bioelectrical signal data and/or audio signal data triggering the emission of the audio sample (e.g., audio signal data including user speech instructions for the emission of a specified audio sample) were collected. Additionally or alternatively, emitting an audio sample can be performed at any suitable time in relation to portions of the method 100, and/or at any suitable time.

However, emitting an audio sample at one or more speakers of the biomonitoring neuroheadset S180 can be performed in any suitable fashion.

The method 100 can, however, include any other suitable blocks or steps configured to collect, monitor, and/or analyze bioelectrical and audio signals of a user with a biomonitoring neuroheadset.

4. System.

As shown in FIGS. 4A-4B, an embodiment of a system 200 for detecting bioelectrical signals and audio signals from a user includes: one or more bioelectrical signal sensors 210 configured to collect bioelectrical signal data from the user; a noise reduction subsystem 220 including one or more reference sensors configured to collect reference signal data contemporaneously with the collection of bioelectrical signal data; a microphone 230 configured to collect an audio signal dataset from the user contemporaneously with the collection of the first bioelectrical signal dataset and the reference signal dataset; a wearable support frame 240 worn at a head region of the user, the wearable support frame 240 supporting and physically connecting the one or more bioelectrical sensors 210 and the one or more reference sensors; and an electronics subsystem 250 including a processing module 252 configured to produce a noise-reduced bioelectrical dataset from processing the bioelectrical signal data with the reference signal data, and to produce a conditioned audio signal dataset from processing the audio signal dataset for transmission with the noise-reduced bioelectrical signal dataset, the electronics subsystem 250 electronically connected to the one or more bioelectrical signal sensors 210, the noise reduction subsystem 220, and the microphone 230.

In some variations, the system 200 can additionally or alternatively include a communications module 254, a speaker 260, a remote processing module 270, and/or a screen separating bioelectrical sensor power wire(s) from microphone power wire(s) to facilitate prevention of cross-talk between corresponding signal data. As shown in FIGS. 6-10, in specific examples of configurations of the system 200, components of the biomonitoring neuroheadset and/or other devices can communicate amongst each other and/or the user.

In some variations, the system 200 and/or components of the system 200 can additionally or alternatively include or communicate data to and/or from: a user database (storing user account information, user profiles, user health records, user demographic information, associated user devices, user preferences, etc.), an analysis database (storing computational models, collected datasets, historical data, public data, simulated data, generated data, generated analyses, diagnostic results, therapy recommendations, etc.), and/or any other suitable computing system.

Figure 6:
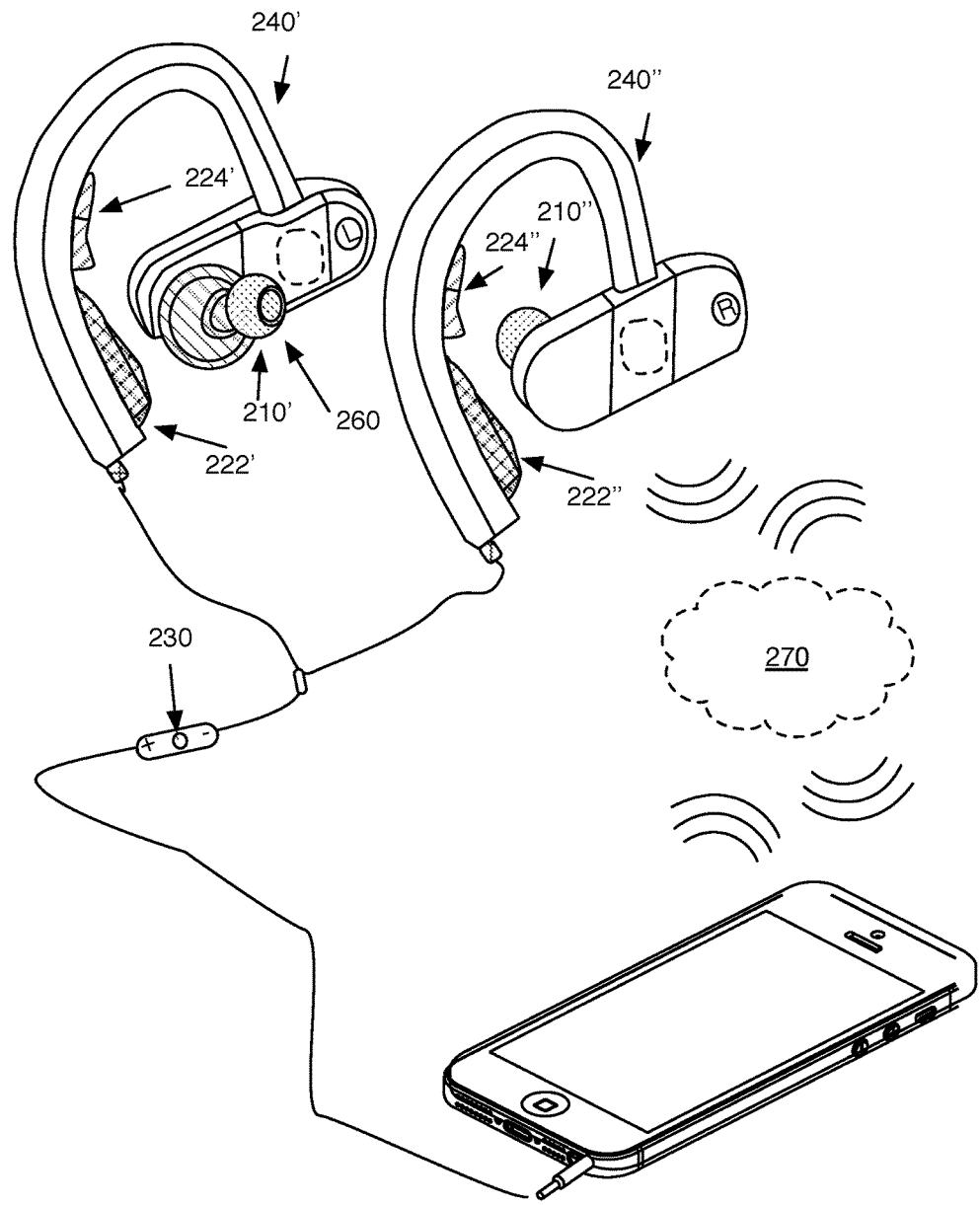
FIG. 6 depicts a graphical representations of a variation of an embodiment of a system for detecting bioelectrical and audio signals of a user.

Database(s) and/or portions of the method 100 can be entirely or partially executed, run, hosted, or otherwise performed by: a remote computing system (e.g., a server, at least one networked computing system, stateless computing system, stateful computing system, etc.), a biomonitoring neuroheadset (e.g., a processing module 252 of a biomonitoring neuroheadset), a user device, a machine configured to receive a computer-readable medium storing computer-readable instructions, or by any other suitable computing system possessing any suitable component (e.g., a graphics processing unit, a communications module 254, etc.). As shown in FIG. 6, in specific examples, the system 200 can include a remote processing module 270 remote from the one or more bioelectrical signal sensor 210, the noise reduction subsystem, the microphone, the wearable support frame, and the electronics subsystem 250. In these specific examples, the remote processing module 270 is preferably configured to identify a blood flow time-varying oscillation in noise-reduced values of a noise-reduced EEG dataset; and estimate at least one of a heart rate and a heart rate variability based on the blood flow time-varying oscillation in noise-reduced values. Additionally or alternatively, the remote processing module 270 can be configured to perform any suitable portion of the method 100. However, the components of the system 200 can be distributed across machine and cloud-based computing systems in any other suitable manner.

Figure 7:
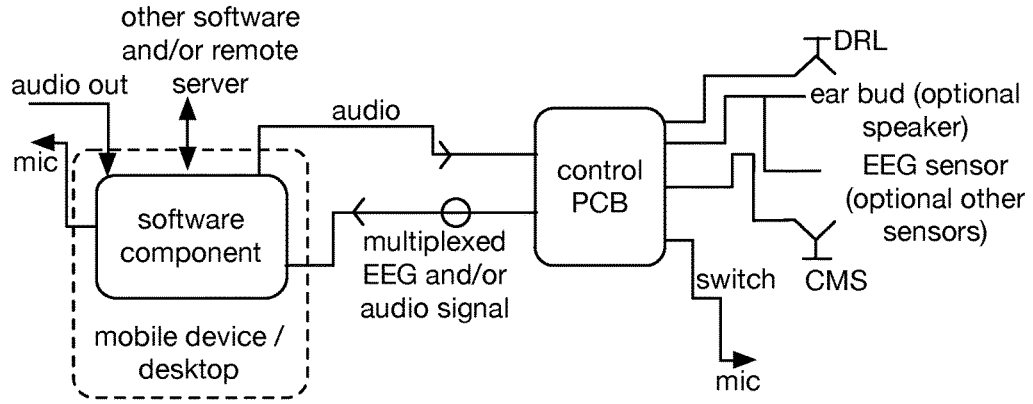
FIGS. 7-11 depict graphical representations of variations of an embodiment of a system for detecting bioelectrical and audio signals of a user.
Figure 8:
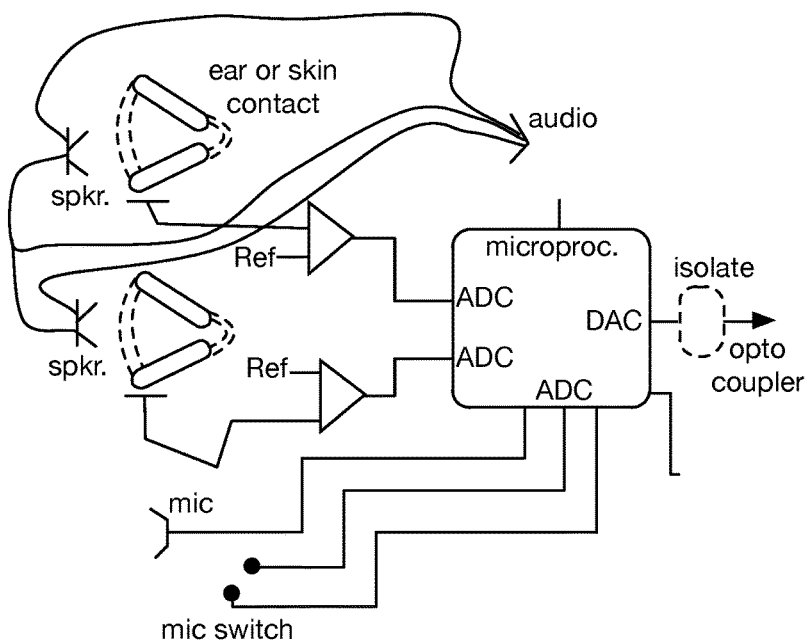
Figure 9:
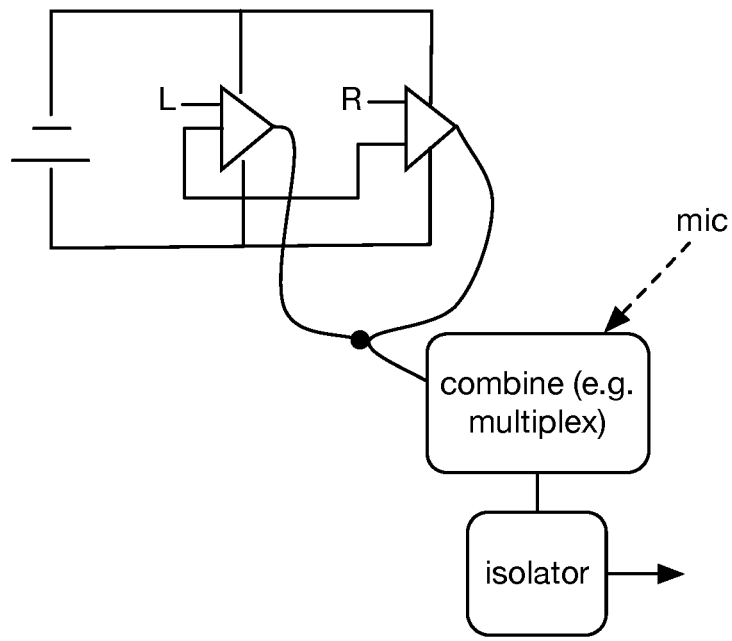
Figure 10:
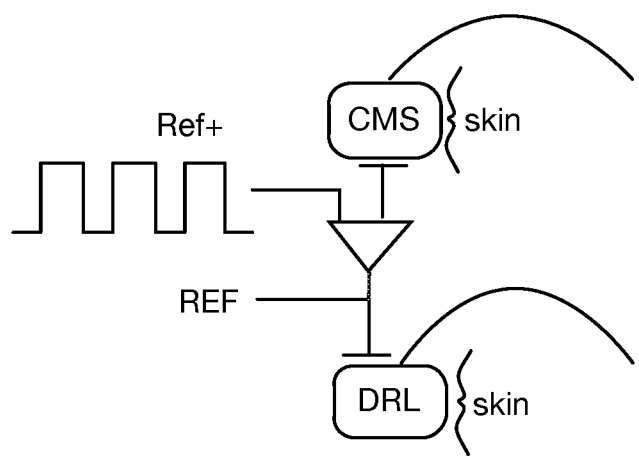
Figure 11:
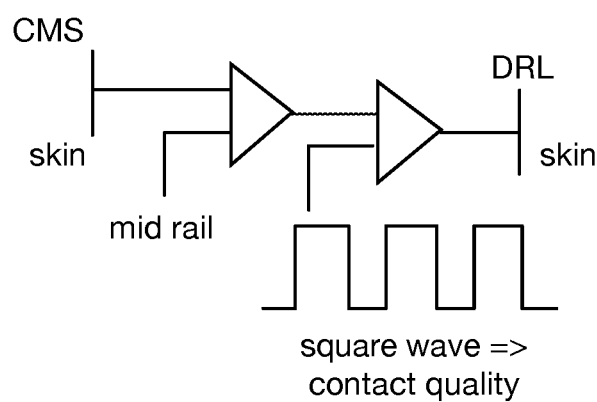

Devices implementing at least a portion of the method 100 can include one or more of: a biomonitoring neuroheadset, smartwatch, smartphone, a wearable computing device (e.g., head-mounted wearable computing device), tablet, desktop, a supplemental biosignal detector, a supplemental sensor (e.g., motion sensors, magnetometers, audio sensors, video sensors, location sensors a motion sensor, a light sensor, etc.), a medical device, and/or any other suitable device. All or portions of the method 100 can be performed by one or more of: a native application, web application, firmware on the device, plug-in, and any other suitable software executing on a device. Device components used with the method 100 can include an input (e.g., keyboard, touchscreen, etc.), an output (e.g., a display), a processor, a transceiver, and/or any other suitable component, wherein data from the input device(s) and/or output device(s) can be generated, analyzed, and/or transmitted to entities for consumption (e.g., for a user to assess their health parameters) Communication between devices and/or databases can include wireless communication (e.g., WiFi, Bluetooth, radiofrequency, etc.) and/or wired communication. As shown in FIGS. 6-7, in variations, communication can be between an electronics subsystem 250 of a biomonitoring neuroheadset and a computing device executing a software component. In variations including wired communication between components of the system 200, the system 200 can additionally or alternatively include a screen (e.g., separating power wires in a cable) configured to prevent cross-talk between collected signals. In a specific example, the system 200 can include: a cable connecting the processing module 252 to one or more EEG sensors 210 and the microphone; an EEG sensor power wire for the one or more EEG sensors, the EEG sensor power wire positioned within the connecting cable; a microphone power wire for the microphone, the microphone power wire positioned within the connecting cable; and a screen separating the EEG sensor power wire from the microphone power wire within the connecting cable, the screen configured to facilitate prevention of cross-talk between the first EEG signal dataset and the audio signal dataset. However, communication between components of the system and/or other devices can be configured in any suitable manner.

Components of the system 200 (e.g., a processing module 252 of an ultrasound system) and/or any other suitable component of the system 200, and/or any suitable portion of the method 100 can employ machine learning approaches including any one or more of: supervised learning (e.g., using logistic regression, using back propagation neural networks, using random forests, decision trees, etc.), unsupervised learning (e.g., using an Apriori algorithm, using K-means clustering), semi-supervised learning, reinforcement learning (e.g., using a Q-learning algorithm, using temporal difference learning), and any other suitable learning style. Each module of the plurality can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked autoencoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm. Each processing portion of the method 100 can additionally or alternatively leverage: a probabilistic module, heuristic module, deterministic module, or any other suitable module leveraging any other suitable computation method, machine learning method or combination thereof.

4.1 Bioelectrical Signal Sensor.

The system 200 can include one or more bioelectrical signal sensors 210, which function to collect bioelectrical signal data from the user. The one or more bioelectrical signal sensor 210 can include one or more bioelectrical signal sensor 210 configured to detect any one or more of: EOG signals, EMG signals, ECG signals, GSR signals, MEG signals, and/or any other suitable signals. Bioelectrical signals can be collected by the one or more bioelectrical signal sensor 210 at any suitable time period. For example, a set of EEG sensors 210 can collect EEG signal datasets contemporaneously during a time period with a set of ECG sensors collecting ECG signal datasets. However, the one or more bioelectrical signal sensor 210 can be configured to collect any suitable signal at any suitable time.

The one or more bioelectrical signal sensor 210 are preferably positioned proximal an ear canal region (e.g., left ear canal, right ear canal) of an ear region of the user, but can additionally or alternatively be positioned at, proximal to, adjacent to, near, distance, and/or with any suitable positional relationship to any suitable ear subregion of an ear region of the user, and/or any suitable anatomical location of the user. In an example, one or more bioelectrical signal sensor 210 can be embedded within in-ear headphones (e.g., used for emitting audio) or on-ear headphones of a biomonitoring neuroheadset. However, bioelectrical signal sensor 210 can be positioned at any suitable location of a biomonitoring neuroheadset.

As shown in FIG. 6, in a variation of the one or more bioelectrical signal sensors 210, the system 200 can include a plurality of EEG sensors 210'. For example, the system 200 can include a first EEG sensor 210' positioned proximal an ear canal (e.g., left ear canal) of the user, the first EEG sensor 210' configured to collect a first EEG signal dataset from the user during a time period; and a second EEG sensor 210" positioned proximal a contralateral ear canal (e.g., a right ear canal) of the user, the second EEG sensor 210" configured to collect a second EEG dataset from the user during the time period. In another example, the first EEG sensor is positioned proximal an elastic cartilage section of the ear canal, and the second EEG sensor is positioned proximal an elastic cartilage section of the contralateral ear canal. Additionally or alternatively, one or more EEG sensors can be positions within, proximal, touching, and/or adjacent to the middle ear and/or inner ear of either the left and/or right ear region. However, the system 200 can include any suitable configuration of a set of EEG sensors 210.

Additionally or alternatively, bioelectrical signal sensor 210 can include any elements described in U.S. application Ser. No. 13/903,832, filed 28 May. 2013, and U.S. patent application Ser. No. 14/447,326 filed 30 Jul. 2014, which are each herein incorporated in their entirety by this reference. However, bioelectrical signal sensors 210 can be configured in any suitable fashion.

4.2 Noise Reduction Module.

The system 200 can include a noise reduction module 220 including one or more reference sensors. The noise reduction module 220 functions to employ one or more reference sensors to collect reference signal data for reducing noise associated with collected bioelectrical signal datasets. A noise reduction module 220 preferably includes one or more common mode sensors 222, but can additionally or alternatively include one or more DRL sensors 224 and/or any other suitable reference sensors.

In relation to reference sensors of the reduction module 220, reference sensors are preferably positioned proximal an ear region of a user (e.g., a temporal bone of a user), but can additionally or alternatively be positioned at, proximal to, adjacent with, and/or distant from any suitable anatomical location of the user. In an example, the system 200 can include a noise reduction subsystem including a reference sensor positioned proximal a mastoid process of a temporal bone proximal the ear canal, the reference sensor configured to collect a reference signal dataset contemporaneously with collection of an EEG signal dataset (e.g., by one or more bioelectrical signal sensor 210) during a first time period. In this example, the reference sensor can be a first common mode sensor 222, where the reference signal dataset is a first common mode signal dataset, where the noise reduction subsystem can further include a driven right leg module positioned proximal the first common mode sensor 222 and the mastoid process of the temporal bone. In this example, the noise reduction subsystem can further include a second common mode sensor 222 positioned proximal a contralateral mastoid process of a contralateral temporal bone proximal the contralateral ear canal, the second common mode sensor 222 configured to collect a second common mode signal dataset. However, reference sensors of the noise reduction module 220 can be configured in any suitable manner.

In a variation of the noise reduction module 220, a set of reference sensors can include, for each ear, one or more common mode sensors 222 and one or more DRL sensors 224 positioned proximal the ear. In a specific example, for a given ear of the user, a corresponding common mode sensor 222 can be positioned proximal a different ear subregion (e.g., a different part of the ear flap) than the corresponding DRL sensor 224. In another variation of the noise reduction module 220, only one type of reference sensor can correspond to an ear of the user. For example, a common mode sensor 222 can be characterized with a primary reference location behind the left ear flap, and a driven right leg sensor can be characterized with a feedback reference location behind a right ear flap. However, any suitable combination of reference sensor types can be arranged at any suitable ear region of a user.

Additionally or alternatively, the noise reduction module 220 can include any elements described in U.S. patent application Ser. No. 14/447,326, filed 30 Jul. 2014, which is hereby incorporated in its entirety by this reference. However, the noise reduction module 220 and the one or more reference sensors can be configured in any suitable fashion.

4.3 Microphone.

The system 200 can include one or more microphones 230, which function to collect an audio signal dataset from the user for use in determining a psychological and/or physiological state of the user. The one or more microphones 230 can be typified by one or more microphone types including dynamic, ribbon, carbon, piezoelectric, condenser, fiber optic, laser, liquid, microelectromechanical systems (MEMS), and/or any other suitable microphone type. The one or more microphones 230 can include any suitable capsule (e.g., with respect to geometry, form, orientation, size, weight, color, materials, etc.) for housing the electrical components of the microphone 230. As shown in FIG. 6, in variations examples, the microphone 230 can be embedded with volume controls for adjusting volume of a speaker 260 of the biomonitoring neuroheadset and/or other suitable component. As shown in FIG. 5B, the microphone 230 can otherwise be omitted from the system 200.

The microphone 230 is preferably configured to collect one or more audio signal datasets from the user contemporaneously with collection of one or more bioelectrical signal datasets and/or reference signal datasets (e.g., during a time period). However, the microphone 230 can be configured to perform any suitable operation.

The microphone 230 is preferably in communication (e.g., wired communication, wireless communication) with a processing module 252 of an electronics subsystem 250 of the biomonitoring neuroheadset, but can additionally or alternatively possess a communication link with any other suitable component of the biomonitoring neuroheadset, the system 200, and/or another device.

As shown in FIGS. 5A and 5C, the microphone 230 is preferably positioned proximal an oral cavity of the user, but can additionally or alternatively be positioned at, proximal to, adjacent to, near, far, and/or with any suitable positional relationship to any anatomical position of the user and/or component of the biomonitoring neuroheadset.

However, the microphone 230 can be configured in any suitable manner.

4.4 Wearable Support Frame.

The system 200 can include one or more wearable support frames 240, which function to provide support for components of the biomonitoring neuroheadset. The one or more wearable support frames 240 preferably support and/or physically connect one or more bioelectrical signal sensor 210 and/or one or more reference sensors. The wearable support frame 240 can possess any suitable dimensions (e.g., width, length, height, surface area, volume, aspect ratio, curvature, etc.). The wearable support frame 240 can include any suitable three-dimensional shapes including: a prism, cube, cylinder, sphere, and/or any suitable three-dimensional shape. The shape of a surface of the wearable support frame 240 can include: a rectangle, square, circle, triangle, polygon, and/or other suitable shape. As shown in FIGS. 4A-4B, 5B-5C, and 6, a wearable support frame 240 can include a primary curvature forming a hook configured to hook around an ear of a user, the era region supporting the wearable support frame 240 on the user. However, one or more wearable support frames 240 can possess any suitable form.

One or more wearable support frames 240 are preferably worn at a head region, but can additionally or alternatively be worn at any suitable anatomical position (e.g., chest region, bones, forehead, etc.) for facilitating mechanical retention of the biomonitoring device to the user. The wearable support frame 240 is preferably mechanically supported at an ear region of the user. In a specific example, the system 200 can include a wearable support frame 240 worn at a head region of the user and cooperatively supported at an ear region proximal the temporal bone and an ear flap of the user, the wearable support frame 240 supporting and physically connecting the EEG sensor 210 and the reference sensor. However, one or more wearable support frames 240 can be positioned at any suitable location and supported by any suitable body region and/or component.

Figure 12:
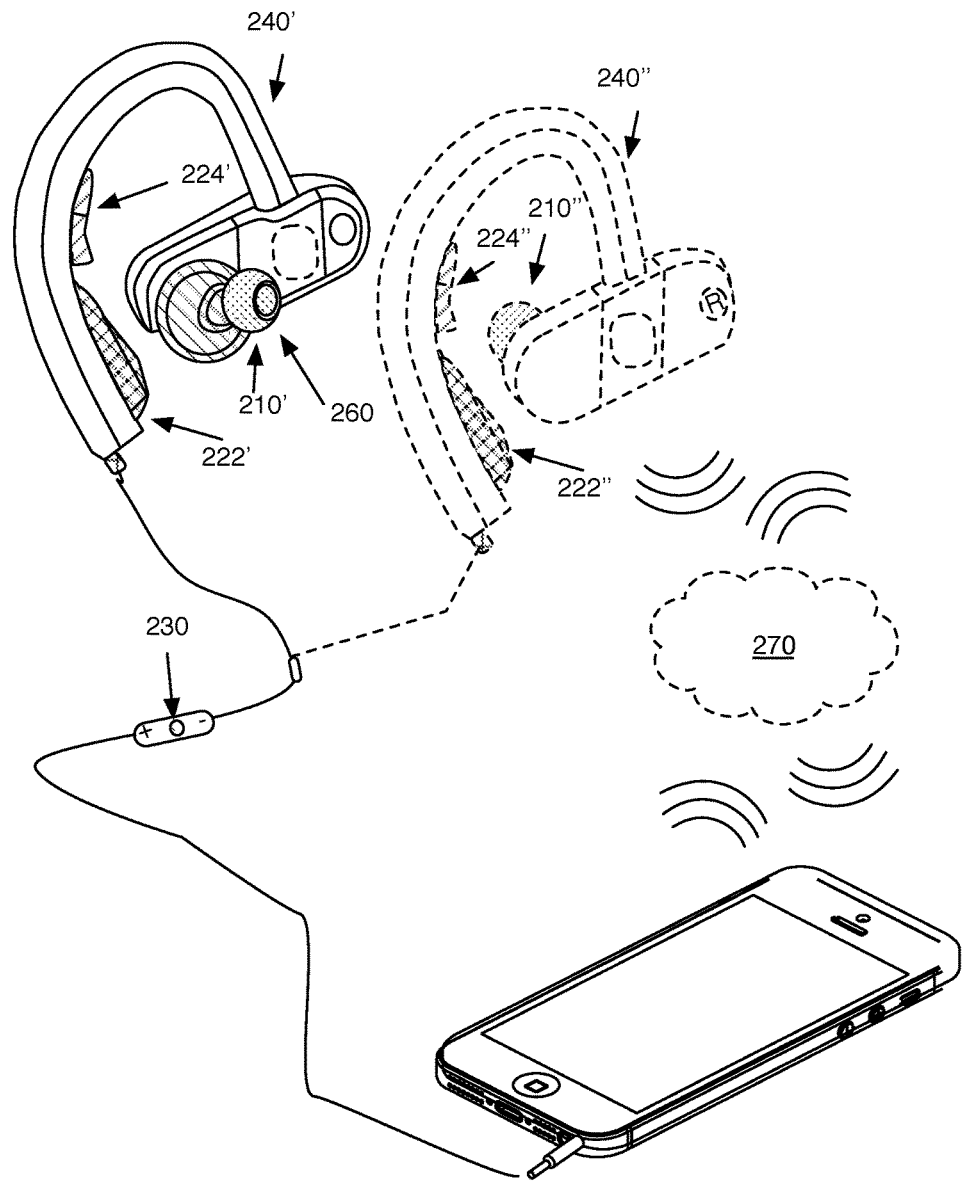
FIG. 12 depicts a graphical representation of a variation of an embodiment of a system for detecting bioelectrical and audio signals of a user.

As shown in FIG. 6, in a variation, the system 200 includes a plurality of wearable support frames 240. For example, the system 200 can include a first wearable support frame 240 240' cooperatively supported at an ear region, the first wearable support frame 240' supporting and physically connecting a first EEG sensor, a first common mode sensor 222', and a first DRL sensor 224' of a DRL module; and a second wearable support frame 240" cooperatively supported at a contralateral ear region, the second wearable support frame 240" supporting and physically connecting a second EEG sensor, a second common mode sensor 222", and a second DRL sensor 224" of a DRL module. Alternatively, as shown in FIG. 12, a biomonitoring neuroheadset can include only a single wearable support frame configured to be worn at a single ear region (e.g., a left ear region or a right ear region) of a user.

However, the one or more wearable support frames 240 can be configured in any suitable fashion.

4.5 Electronics Subsystem.

As shown in FIG. 4B, the system 200 can include an electronics subsystem 250, which functions to receive, process, and/or transmit signals collected by one or more bioelectrical signal sensor 210, reference sensors, and/or a microphone 230. The electronics subsystem 250 can additionally or alternatively include a processing module 252 and/or a communications module 254. However, the electronics subsystem 250 can include any other suitable modules configured to facilitate signal reception, signal processing, and/or data transfer in an efficient manner.

The electronics subsystem 250 is preferably electronically connected to the one or more bioelectrical signal sensors 210, the noise reduction subsystem 220, and the microphone 230, but can additionally or alternatively be connected (e.g., wired connection, wireless connection) to any suitable component of the biomonitoring neuroheadset, and/or any suitable component.

Components of the electronics subsystem 250 are preferably embedded within one or more wearable support frames 240 of the biomonitoring neuroheadset, but can be otherwise located at the biomonitoring neuroheadset and/or other component.

However, the electronics subsystem 250 can be configured in any suitable manner.

4.5.A Processing Module.

As shown in FIG. 4B, the electronics subsystem 250 can include a processing module 252 functioning to process collected and/or received datasets. The processing module 252 can additionally or alternatively function to control notifications to a user, generate a health parameter, generate operation instructions for a user device, and/or perform any other suitable operations related to the method 100. The processing module 252 can include one or more: microcontrollers, central processing units (CPU), a microprocessors, digital signal processors (DSP), a state machine, an application-specific integrated circuit (ASIC), a programmable logic device (PLD), a field programmable gate array (FPGA), a graphics processing unit (GPU), any other suitable processing device. The processing module 252 preferably includes one or more printed circuit boards (PCBs), which can preferably satisfy the data collection and/or processing requirements associated with the method 100. In a specific example, the electronics subsystem 250 includes a control PCB embedded in a wearable support frame 240 configured to hook onto an ear region of the user. In another specific example, the electronic subsystem includes a set of daughter PCBs, where at least one daughter PCB is embedded in each of a plurality of wearable support frames 240 (e.g., a wearable support frame 240 for each ear). In another specific example, the electronics submodule can include a first processing submodule (e.g., a control PCB, a daughter PCB, etc.) positioned proximal a first EEG sensor, and a second processing submodule (e.g., a control PCB, a daughter PCB, etc.) positioned proximal a second EEG sensor. However, the processing module 252 can include any suitable components.

The processing module 252 is preferably configured to produce a noise-reduced EEG dataset from processing one or more EEG signal datasets with one or more reference signal datasets, and to produce a conditioned audio signal dataset from processing one or more audio signal datasets for transmission with the noise-reduced EEG dataset. The processing module 252 can be additionally or alternatively configured to control data collection parameters for collection of bioelectrical signal datasets, reference signal datasets, and/or audio signal datasets. Data collection parameters can include: sampling frequency, time of sampling, time between samples, amount of data to collect, types of data to collect, conditions for triggering collection, and/or any suitable data collection parameter. However, the processing module 252 can be configured to perform any suitable portion of the method 100

Additionally or alternatively, the processing module 252 can be configured in any suitable manner.

4.5.B Communications Module.

As shown in FIG. 4B, the electronics subsystem 250 can include a communications module 254 functioning to receive and/or transmit data (e.g., a combined audio signal and bioelectrical signal dataset) with a remote server, a user device, and/or any suitable component. The communication submodule preferably includes a transmitter, and can additionally or alternatively include a receiver. In a variation, the communication module can facilitate wired communication between the biomonitoring neuroheadset and another device (e.g., a smartphone of a user). In this variation, wired communication can be through a cable with connectivity for an audio jack, USB, mini-USB, lightning cable, and/or any suitable wired connection medium. In another variation, the communication module can facilitate wireless communication between the biomonitoring neuroheadset and another device. Wireless communication can be facilitated through Zigbee, Z-wave, WiFi, but can additionally or alternatively be facilitated through short-range wireless communication including Bluetooth, BLE beacon, RF, IR, or any other suitable wireless communication medium.

The communications module 254 is preferably configured to communications module 254 of the electronics subsystem 250, the communications module 254 configured to transmit any suitable dataset (e.g., a bioelectrical signal dataset, an audio signal dataset, a combined bioelectrical signal and audio signal dataset, etc.) to any suitable device. In a specific example, the communications module 254 can be configured to transmit the noise-reduced EEG dataset to the mobile computing device for transmission to a remote processing module 270, and/or to transmit the audio signal dataset to a mobile computing device of the user, wherein the audio signal dataset specifies instructions for controlling operation of the mobile computing device. However, the communications module 254 can be configured to perform any suitable operation.

The communication submodule can additionally or alternatively include a router (e.g., a WiFi router), an extender for one or more communication protocols, a communication protocol translator, or include any other suitable communication submodule. The communication submodule can also additionally or alternatively include or be communicatively coupled to RAMs, ROMs, flash memory, EEPROMs, optical devices (CD or DVD), hard drives, floppy drives, and/or any suitable data storage device However, the communication submodule can receive, convert, and/or transmit any type of suitable signal or data to any suitable component or device.

4.6 Speaker.

The system 200 can include one or more speaker 260 of a biomonitoring neuroheadset. The speaker 260 functions to output audio to promote a therapy and/or facilitate physiological and/or psychological monitoring (e.g., a user response to the outputted audio) of the user. The speaker 260 is preferably embedded with a biomonitoring neuroheadset. In particular, the speaker 260 is preferably embedded in an ear bud physically supported by the wearable support frame 240 and additionally housing portions one or more bioelectrical signal sensor 210. In a specific example, the system 200 can include a speaker 260 positioned proximal an EEG sensor 210 and an ear canal of the user. Additionally or alternatively, one or more speakers 260 can be positioned at any location in relation to components of the biomonitoring neuroheadset. However, the speaker 260 can be remote from the biomonitoring neuroheadset (e.g., a speaker 260 wirelessly communicating with the biomonitoring neuroheadset), or can otherwise be omitted from the system 200.

The speaker 260 is preferably controlled by the processing module 252 of the electronics subsystem 250, but can additionally or alternatively be controlled by any suitable component. The speaker 260 can be configured to emit audio samples generated by and/or transmitted by any suitable user device. In a specific example, the communications module 254 of the electronics subsystem 250 can be configured to receive from a mobile computing device an audio sample transmitted based on instructions extracted from a collected audio signal input of the user, where the speaker 260 can be configured to emit the audio sample.

In a variation, the one or more speakers 260 can be configured to emit one or more audio samples from which a user response can be measured (e.g., by a bioelectrical signal sensor 210, by a microphone 230). In a specific example, one or more EEG sensors 210 can be configured to collect a second EEG signal dataset (e.g., where a first EEG signal dataset was collected prior to emission of the audio sample) from the user during a time period in response to emission of the audio sample, and wherein one or more reference sensors are further configured to collect a second reference signal dataset (e.g., where the first reference signal dataset was collected prior to emission of the audio sample) from the user contemporaneously with collection of the second EEG signal dataset during the time period.

However, one or more speakers 260 can be configured in any suitable manner.

4.7 Supplemental Sensors.

The system 200 can include one or more supplemental sensors, which function to collect supplemental data to aid in monitoring psychological (e.g., cognitive state metric) and/or physiological status (e.g., cardiovascular parameters, health status parameter, etc.) of a user. One or more supplemental sensors can include: motion sensors (e.g., accelerometers, gyroscopes), magnetometers, audio sensors, video sensors, location sensors, and/or any other suitable sensor. A supplemental sensor is preferably arranged at a suitable location of the biomonitoring neuroheadset, but can additionally or alternatively be positioned at any suitable location (e.g., as part of user device distinct from the biomonitoring neuroheadset, etc.). However, one or more supplemental sensors can be configured in any suitable manner.

In a specific example, one or more supplemental sensors can include a motion sensor configured to detect one or more user motion features indicating a user's gait, imbalance, tremors, exercise habits, counting steps, movement restrictions, and/or any other suitable user motion feature. User motion features and/or any suitable data collected by one or more supplemental sensors can be used with, combined with, and/or processed in any suitable manner with collected bioelectrical signal data and/or other suitable datasets in order to determine a health parameter (e.g., cognitive state metric, cardiovascular parameter such as heart beat, etc.), control operation of a user device (e.g., detecting user gestural instructions such as nodding, head shaking, control taps on casing, head motion, body motion, facial expressions, etc.), and/or perform any other suitable operation in relation to the method 100. However, one or more supplemental sensors can be configured to perform any suitable operation.

The method 100 and/or system 200 of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the embodiments of the invention without departing from the scope of this invention as defined in the following claims.

We claim:

1. A method for detecting bioelectrical signals and audio signals from a user, comprising:
    establishing bioelectrical contact between a first subregion of an ear region of the user and a first electroencephalogram (EEG) sensor of a biomonitoring neuroheadset;
    establishing bioelectrical contact between a second subregion of the ear region of the user and a first common mode sensor of a noise reduction subsystem of the biomonitoring neuroheadset, wherein the first subregion is proximal the second subregion, and wherein the first EEG sensor is proximal the first common mode sensor;
    collecting, at the first EEG sensor, a first EEG signal dataset from the user during a first time period;
    collecting, at the first common mode sensor, a first common mode signal dataset contemporaneously with collecting the first EEG signal dataset during the first time period;
    collecting, at a microphone of the biomonitoring neuroheadset, a first audio signal dataset from the user contemporaneously with collecting the first EEG signal dataset and the first common mode signal dataset during the first time period;
    generating a first combined audio and EEG processed dataset, comprising:
        producing a common noise-reduced EEG dataset from the first EEG signal dataset and the first common mode signal dataset,
        producing a conditioned audio signal dataset from processing the first audio signal dataset for transmission with the common noise-reduced EEG dataset, and
        generating the first combined audio and EEG processed dataset from the common noise-reduced EEG dataset and the conditioned audio signal dataset;
    receiving, at a remote server, a common noise-reduced EEG signal portion and an audio signal portion of the first combined audio and EEG processed dataset;
    generating a cognitive state metric based at least on the common noise-reduced EEG signal portion and the audio signal portion, wherein the cognitive state metric indicates a cognitive state of the user during the first time period;

determining an audio therapy to modify the cognitive state of the user, based on the cognitive state metric; and promoting, at a speaker of the biomonitoring neuroheadset, the audio therapy to the user.

2. The method of claim 1, wherein generating the first combined audio and EEG processed dataset comprises generating a driven right leg signal using a driven right leg module characterized by a first feedback reference location at a third subregion of the ear region, the third subregion proximal the first and the second subregions of the ear region, wherein the noise reduction subsystem comprises the driven right leg module, and wherein producing the common noise-reduced EEG dataset further comprises producing the common noise-reduced EEG dataset from the driven right leg signal.

3. The method of claim 2, further comprising:
establishing bioelectrical contact between a first contralateral subregion of a contralateral ear region of the user and a second EEG sensor of the biomonitoring neuroheadset;
establishing bioelectrical contact between a second contralateral subregion of the contralateral ear region of the user and a second common mode sensor of a noise reduction subsystem of the biomonitoring neuroheadset, wherein the first contralateral subregion is proximal the second contralateral subregion, and wherein the second EEG sensor is proximal the second common mode sensor;
collecting, at the second EEG sensor, a second EEG signal dataset contemporaneously with collecting the first EEG signal dataset, the first common mode signal dataset, and the audio signal dataset during the first time period;
collecting, at the second common mode sensor, a second common mode signal dataset contemporaneously with collecting the first and the second EEG signal datasets, the first common mode signal dataset, and the audio signal dataset during the first time period, wherein producing the common noise-reduced EEG dataset further comprises producing the common noise-reduced EEG dataset from the second EEG signal dataset and the second common mode signal dataset.

4. The method of claim 3, wherein the first subregion comprises an ear canal of the user, wherein the first contralateral subregion comprises a contralateral ear canal of the user, wherein the second subregion comprises an ear subregion proximal a mastoid process of a temporal bone of the user, and wherein the second contralateral subregion comprises a contralateral ear subregion proximal a contralateral mastoid process of a contralateral temporal bone of the user.

5. The method of claim 3, wherein generating the first combined audio and EEG processed dataset comprises generating an averaged common mode signal dataset from performing an averaging operation with the first common mode signal dataset and the second common mode signal dataset, and wherein producing the common noise-reduced EEG dataset comprises producing the common noise-reduced EEG dataset from the averaged common mode signal dataset.

6. The method of claim 3, wherein the driven right leg module is further characterized by a second feedback reference location at a third contralateral subregion of the contralateral ear region, the third contralateral subregion proximal the first and the second contralateral subregions of the contralateral ear region, wherein generating the driven right leg signal is in response to adequate contact between the user and the driven right leg module at least at one of the first feedback reference location and the second feedback reference location.

7. The method of claim 1, further comprising:
applying a reference signal to the user at the ear region with the first common mode sensor during a second time period;
in response to applying the reference signal, collecting, at the first EEG sensor, a contact quality dataset during the second time period; and
evaluating a quality of the bioelectrical contact between the first subregion of the ear region and the first EEG sensor, based on the contact quality dataset.

8. The method of claim 1, further comprising:
transmitting the first combined audio and EEG processed dataset to a computing device of the user;
generating, at a software component executing on the computing device, an analysis of an audio signal portion of the first combined audio and EEG processed dataset;
receiving, at the biomonitoring neuroheadset, operation instructions transmitted by the computing device and generated based on the analysis of the audio signal portion; and
operating the biomonitoring neuroheadset based on the operation instructions.

9. The method of claim 1, further comprising:
in response to promoting the audio therapy to the user at the speaker:
collecting, at the first EEG sensor, a second EEG signal dataset from the user during a second time period;
collecting, at the first common mode sensor, a second common mode signal dataset contemporaneously with collecting the second EEG signal dataset during the second time period;
collecting, at the microphone, a second audio signal dataset from the user contemporaneously with collecting the second EEG signal dataset and the second common mode signal dataset during the second time period; and
generating a second combined audio and EEG processed dataset based on the second EEG signal dataset, the second common mode signal dataset, and the second audio signal; and
generating a second cognitive state metric based on the second combined audio and EEG processed dataset, wherein the second cognitive state metric indicates a cognitive state response to the audio therapy during the second time period.

10. The method of claim 1, further comprising:
identifying a blood flow time-varying oscillation in noise-reduced values of the common noise-reduced EEG dataset; and
estimating at least one of a heart rate and a heart rate variability based on the blood flow time-varying oscillation in the noise-reduced values, wherein the at least one of the heart rate and the heart rate variability corresponds to the first time period.

11. The method of claim 10, wherein identifying the blood flow time-varying oscillation in noise-reduced values comprises identifying a set of QRS complex sequences in the noise-reduced values of the common noise-reduced EEG dataset, and wherein estimating the at least one of the heart rate and the heart rate variability is based on the set of QRS complex sequences.

12. The method of claim 10, further comprising generating the cognitive state metric for the user based on the common-noise reduced EEG signal portion, the audio signal portion, and the at least one of the heart rate and the heart rate variability.

13. A system for detecting bioelectrical signals and audio signals from a user, comprising:
   a first EEG sensor configured to be positioned proximal an ear canal of the user, the first EEG sensor configured to collect a first EEG signal dataset from the user during a first time period;
   a noise reduction subsystem comprising a reference sensor configured to be positioned proximal a mastoid process of a temporal bone proximal the ear canal, the reference sensor configured to collect a reference signal dataset contemporaneously with collection of the first EEG signal dataset during the first time period;
   a microphone configured to be positioned proximal an oral cavity of the user, the microphone configured to collect an audio signal dataset from the user contemporaneously with collection of the first EEG signal dataset and the reference signal dataset during the first time period;
   a wearable support frame configured to be worn at a head region of the user and cooperatively supported at an ear region proximal the temporal bone and an ear flap of the user, the wearable support frame supporting and physically connecting the EEG sensor and the reference sensor;
   an electronics subsystem comprising a processing module system configured to produce a noise-reduced EEG dataset from processing the first EEG signal dataset with the reference signal dataset, and to produce a conditioned audio signal dataset from processing the audio signal dataset for transmission with the noise-reduced EEG dataset, the electronics subsystem electronically connected to the first EEG sensor, the noise reduction subsystem, and the microphone;
   a remote processing module remote from the first EEG sensor, the noise reduction subsystem, the microphone, the wearable support frame, and the electronics subsystem; and
   a communications module of the electronics subsystem, the communications module configured to:
      transmit the noise-reduced EEG dataset to a mobile computing device for transmission to the remote processing module, and
      transmit the audio signal dataset to the mobile computing device, wherein the audio signal dataset specifies instructions for controlling operation of the mobile computing device.

14. The system of claim 13, wherein the reference sensor is a first common mode sensor, wherein the reference signal dataset is a first common mode signal dataset, wherein the noise reduction subsystem further comprises a driven right leg module configured to be positioned proximal the first common mode sensor and the mastoid process of the temporal bone, and wherein the processing module is further configured to produce the noise-reduced EEG dataset from a driven right leg dataset generated from using the driven right leg module and the first common mode signal dataset.

15. The system of claim 14, wherein the system further comprises a second EEG sensor configured to be positioned proximal a contralateral ear canal of the user, the second EEG sensor configured to collect a second EEG dataset from the user during the first time period, wherein the noise reduction subsystem further comprises a second common mode sensor configured to be positioned proximal a contralateral mastoid process of a contralateral temporal bone proximal the contralateral ear canal, the second common mode sensor configured to collect a second common mode signal dataset, and wherein the processing module system is further configured to produce the noise-reduced EEG dataset from the second EEG signal dataset and a combined common mode signal dataset generated from combining the first and the second common mode signal datasets.

16. The system of claim 15, wherein the processing module system comprises:
   a first processing module positioned proximal the first EEG sensor, and
   a second processing module positioned proximal the second EEG sensor.

17. The system of claim 13, wherein the remote processing module system is configured to:
   identify a blood flow time-varying oscillation in noise-reduced values of the noise-reduced EEG dataset; and
   estimate at least one of a heart rate and a heart rate variability based on the blood flow time-varying oscillation in the noise-reduced values.

18. The system of claim 13,
   wherein the communications module is further configured to receive from the mobile computing device an audio sample transmitted based on the specified instructions, the system further comprising a speaker configured to be positioned proximal the first EEG sensor and the ear canal of the user, the speaker configured to emit the audio sample,
   wherein the first EEG sensor is configured to collect a second EEG signal dataset from the user during a second time period in response to emission of the audio sample, and
   wherein the reference sensor is further configured to collect a second reference signal dataset from the user contemporaneously with collection of the second EEG signal dataset during the second time period.

19. The system of claim 13, further comprising:
   a cable connecting the processing module to the first EEG sensor and the microphone;
   an EEG sensor power wire for the first EEG sensor, the EEG sensor power wire positioned within the connecting cable;
   a microphone power wire for the microphone, the microphone power wire positioned within the connecting cable; and
      a screen separating the EEG sensor power wire from the microphone power wire within the connecting cable, the screen configured to facilitate prevention of cross-talk between the first EEG signal dataset and the audio signal dataset.

20. A method for detecting bioelectrical signals and audio signals from a user, comprising:
   establishing bioelectrical contact between a first subregion of an ear region of the user and a first electroencephalogram (EEG) sensor of a biomonitoring neuroheadset;
   establishing bioelectrical contact between a second subregion of the ear region of the user and a first common mode sensor of a noise reduction subsystem of the biomonitoring neuroheadset, wherein the first subregion is proximal the second subregion, and wherein the first EEG sensor is proximal the first common mode sensor;
   collecting, at the first EEG sensor, a first EEG signal dataset from the user during a first time period;

collecting, at the first common mode sensor, a first common mode signal dataset contemporaneously with collecting the first EEG signal dataset during the first time period;

collecting, at a microphone of the biomonitoring neuroheadset, a first audio signal dataset from the user contemporaneously with collecting the first EEG signal dataset and the first common mode signal dataset during the first time period; and generating a first combined audio and EEG processed dataset, comprising:
  producing a common noise-reduced EEG dataset from the first EEG signal dataset and the first common mode signal dataset,
  producing a conditioned audio signal dataset from processing the first audio signal dataset for transmission with the common noise-reduced EEG dataset, and
  generating the first combined audio and EEG processed dataset from the common noise-reduced EEG dataset and the conditioned audio signal dataset;

transmitting the first combined audio and EEG processed dataset to a computing device of the user;

generating, at a software component executing on the computing device, an analysis of an audio signal portion of the first combined audio and EEG processed dataset;

receiving, at the biomonitoring neuroheadset, operation instructions transmitted by the computing device and generated based on the analysis of the audio signal portion; and operating the biomonitoring neuroheadset based on the operation instructions.

* * * * *

UNITED STATES PATENT AND TRADEMARK OFFICE
CERTIFICATE OF CORRECTION

PATENT NO. : 10,291,977 B2  
APPLICATION NO. : 15/209582  
DATED : May 14, 2019  
INVENTOR(S) : Mackellar et al.

Page 1 of 1

It is certified that error appears in the above-identified patent and that said Letters Patent is hereby corrected as shown below:

In the Claims

Column 28, Line 33, Claim 1 delete "neuroheadset ," and insert --neuroheadset,-- therefor  
Column 31, Line 1, Claim 12 delete "common-noise reduced" and insert --common noise-reduced-- therefor  
Column 32, Line 62, Claim 20 delete "neuroheadset ," and insert --neuroheadset,-- therefor Signed and Sealed this  
Twenty-fifth Day of February, 2020

Andrei Iancu  
*Director of the United States Patent and Trademark Office*